US012751389B2

(12) United States Patent
Nakamura et al.

(10) Patent No.: US 12,751,389 B2

(45) Date of Patent: Oct. 6, 2026

(54) SPINACH PLANT HAVING NOVEL DOWNY MILDEW RESISTANCE GENE

(71) Applicant: SAKATA SEED CORPORATION, Yokohama (JP)

(72) Inventors: Yo Nakamura, Yokohama (JP); Ryo Kimura, Yokohama (JP); Yuichi Sugihara, Yokohama (JP); Yosuke Moritama, Yokohama (JP)

(73) Assignee: Sakata Seed Corporation, Kanagawa (JP)

( * ) Notice: Subject to any disclaimer, the term of this patent is extended or adjusted under 35 U.S.C. 154(b) by 134 days.

(21) Appl. No.: 18/705,369

(22) PCT Filed: Nov. 1, 2022

(86) PCT No.: PCT/JP2022/040890

§ 371 (c)(1),
(2) Date: Apr. 26, 2024

(87) PCT Pub. No.: WO2023/074911

PCT Pub. Date: May 4, 2023

(65) Prior Publication Data

US 2025/0234825 A1 Jul. 24, 2025

(30) Foreign Application Priority Data

Nov. 1, 2021 (JP) ................................ 2021-178897

(51) Int. Cl.

*A01H 1/04* (2006.01)
*A01H 1/00* (2006.01)
*C12Q 1/6895* (2018.01)

(52) U.S. Cl.

CPC ........... *A01H 1/045* (2021.01); *A01H 1/1255* (2021.01); *C12Q 1/6895* (2013.01); *C12Q 2600/13* (2013.01)

(58) Field of Classification Search

CPC ...................................................... A01H 1/045
See application file for complete search history.

(56) References Cited

U.S. PATENT DOCUMENTS

| | | | |
|---|---|---|---|
| 9,974,276 B2 | 5/2018 | Feitsma et al. | |
| 10,258,001 B2 | 4/2019 | Dijkstra et al. | |
| 10,258,002 B2 | 4/2019 | Dijkstra et al. | |
| 2019/0104700 A1 | 4/2019 | Feitsma et al. | |
| 2020/0367460 A1* | 11/2020 | Koerber | A01H 1/045 |

FOREIGN PATENT DOCUMENTS

| | | | | |
|---|---|---|---|---|
| CN | 107541551 A | 1/2018 | | |
| CN | 107541554 A | 1/2018 | | |
| JP | 6457269 B | 1/2019 | | |
| JP | 6684207 B | 4/2020 | | |
| WO | 2015/036378 A1 | 3/2015 | | |
| WO | WO-2015054339 A1 * | 4/2015 | C12Q 1/6895 | |
| WO | 2018/059651 A1 | 4/2018 | | |
| WO | 2019/145446 A1 | 8/2019 | | |
| WO | 2019/145447 A1 | 8/2019 | | |
| WO | 2020/239215 A1 | 12/2020 | | |

OTHER PUBLICATIONS

Supplementary European Search Report issued in corresponding EP Application No. 22887236, mailed on Sep. 15, 2025.

Chunda Feng et al: "New Races and Novel Strains of the Spinach Downy Mildew Pathogen *Peronospora effusa*", Plant Disease, vol. 102, No. 3, Jan. 23, 2018 (Jan. 23, 2018), pp. 613-618, XP055652623, US ISSN: 0191-2917, DOI: 10.1094/PDIS-05-17-0781-RE [retrieved on Aug. 14, 2025].

Plantum, "Denomination of Pe: 18 and 19, two new races of downy mildew in spinach", [ online ] , Apr. 15, 2021, < URL:https://plantum.nl/denomination-of-pe-18-and-19-two-new-races-of-downy-mildew-in-spinach/ >.

Correll et al., Spinach: better management of downy mildew and white rust through genomics, European Journal of Plant Pathology, 2011, vol. 129, pp. 193-205.

Feng et al., Development of molecular markers linked to three spinach downy mildew resistance loci, Euphytica, 2018, 214:174.

International Seed Federation, "Differential Sets Peronospora farinosa f. sp. *spinaciae* (P. effusa)", 2018 < URL:https://www.worldseed.org/wp-content/uploads/2018/04/Spinach-downy-mildew_April2018.pdf>.

Iwata et al., AntMap: Constructing Genetic LinKage Maps Using an Ant Colony Optimization Algorithm, Breeding Science, 2006, vol. 56(4), pp. 371-377.

* cited by examiner

*Primary Examiner* — Bratislav Stankovic

(74) *Attorney, Agent, or Firm* — Honigman LLP; Jeffrey I. Lehrberg; Jonathan P. O'Brien

(57) ABSTRACT

The present invention provides a spinach plant having resistance to a broad range of races, a method for producing said spinach plant, and the like. The present invention provides a downy mildew resistant spinach plant having a downy mildew resistance RPF-SK1 gene in at least one allele, wherein in the RPF-SK1 gene: (a) the SNP identified by chr3_1215815 is cytosine, (b) the SNP identified by chr3_1215855 is thymine, (c) the SNP identified by chr3_1216014 is cytosine, (d) the SNP identified by chr3_1216093 is guanine, the SNP identified by chr3_1216094 is guanine, and the SNP identified by chr3_1216095 is adenine, (e) the SNP identified by chr3_1216288 is adenine, or (f) the SNP identified by chr3_1216291 is guanine.

15 Claims, 5 Drawing Sheets

Specification includes a Sequence Listing.

*FIG. 1D*

```
           1  TCAGATTAAATATATGGGAAATGTAAGTTAATTGGGGATGCACATAAGGTGTTTGATGAAATGTCTATTAGAAATGTTGTTTCTTGGACTTAGAATGATATACACTGTCGTCCTTTGGTTTC
         ┌ 2  TCAGATTAAATATATGGGAAATGTAAGTTAGTTGGGGATGCACATAAGGTGTTTGATGAAATGTCTATGAGAAATGTTGTTTCTTGGACTTAGAATGATATACACTGTCGTCCTT-------
         │ 3  TCAGATTAAATATATGGGAAATGTAAGTTAATTGGGGATGCACATAAGGTGTTTGATGAAATGTCTATTAGAAATGTTGTTTCTTGGACTTAGAATGATATACACTGTCGTCCTTTGGTTTC
         │ 4  TCAGATTAAATATATGGGAAATGTAAGTTAATTTGGATGCACATAAGGTGTTTGCTGAAATGTCTATGAGAAATGTTGTTTCTTGGACTTAGAATGATATACACTGTCGTCCATTGGTTTC
WOLF_β  ┤ 5  --------------------------------------------------------------------------------------------------------------------------
         │ 6  --------------------------------------------------------------------------------------------------------------------------
         │ 7  -------------------------------------------------------------------------------TTTCTTAGA----------------------------------
         └ 8  TCAGATTAAATATATGGGAAATGTAAGTTAATTGGGGATGCACATAAGGTGTTTGATGAAATGTCTATTAGAAATGTTGTTTCTTGGACTTAGAATGATATACACTGTCGTCCTTTGGTTTC
           9  TCAGATTAAATATATGGGAAATGTAAGTTAGTTGGGGATGCACATAAGGTGTTTGATGAAATGTCTATTAGAAATGTTGTTTCTTGGACTTAGAATGATATACACTGTCGTCCTTTGGTTTC
         ┌ 10 TCAGATTAAATATATGGGAAATGTAAGTTAGTTGGGGATGCACATAAGGTGTTTGATGAAATGTCTATTAGAAATGTTGTTTCTTGGACTTAGAATGATATACACTGTCGTCCTTTGGTTTC
         │ 11 TCAGATTAAATATATGGGAAATGTAAGTTAGTTGGGGATGCACATAAGGTGTTTGATG-----------------------------------------------------------GTTTC
         │ 12 TCAGATTAAATATATGGGAAATGTAAGTTAATTGGGGATGCACATAAGGTGTTTGATGAAATGTCTATGAGAAATGTTGTTTCTTGGACTTAGAATGATATACACTGTCGTCCTTTGGTTTC
         │ 13 TCAGATTAAATATATGGGAAATGTAAGTTAATTTGGATGCACATAAGGTGTTTGCTGAAATGTCTATGAGAAATGTTGTTTCTTGGACTTAGAATGATATACACTGTCGTCCATTGGTTTC
         │ 14 TCAGATTAAATATATGGGAAATGTAAGTTAATTGGGGATGCACATAAGGTGTTTGATGAAATGTCTATTAGAAATGTTGTTTCTTGGACTTAGAATGATATACACTGTCGTCCTTTGGTTTC
         │ 15 TCAGATTAAATATATGGGAAATGTAAGTTAATTGGGGATGCACATAAGGTGTTTGATGAAATGTCTATGAGAAATGTTGTTTCTTGGACTTAGAATGATATACACTGTCGTCCTTTGGTTTC
         │ 16 TCAGATTAAATATATGGGAAATGTAAGTTAATTTGGATGCACATAAGGTGTTTGCTGAAATGTCTATGAGAAATGTTGTTTCTTGGACTTAGAATGATATACACTGTCGTCCATTGGTTTC
         │ 17 TCAGATTAAATATATGGGAAATGTAAGTTAATTTGGATGCACATAAGGTGTTTGCTGAAATGTCTATGAGAAATGTTGTTTCTTGGACTTAGAATGATATACACTGTCGTCCATTGGTTTC
WOLF_α  ┤ 18 TCAGATTAAATATATGGGAAATGCAAGTTAATTTGGATGCACATAAGGTGTTTGCTGAAATGTCTATGAGAAATGTTGTTTCTTGGACTTAGAATGATATACACTGTCGTCCTTTGGTTTC
         │ 19 TCAGATTAAATATATGGAAAATGTAAGTTAGTTGGGGATGCACATAAGGTGTTTGATGAAATGTCTTTTAGAAATGTTGTTTCTTGGACTTAGAATGATATACACTGTCGTCCTTTGGTTTC
         │ 20 TCAGATTAAATATATGGAAAATGTAAGTTAGTTGGGGATGCACATAAGGTGTTTGATGAAATGTCTATTAGAAATGTTGTTTCTTGGACTTAGAATGATATACACTGTCGTCCTTTGGTTTC
         │ 21 TCAGATTAAATATATGGAAAATGTAAGTTAGTTGGGGATGCACATAAGGTGTTTGATGAAATGTCTATTAGAAATGTTGTTTCTTGGACTTAGAATGATATACACTGTCGTCCTTTGGTTTC
         │ 22 TCAGATTAAATATATGGGAAATGTAAGTTAATTTGGATGCACATAAGGTGTTTGCTGAAATGTCTATGAGAAATGTTGTTTCTTGGACTTAGAATGATATACACTGTCGTCCATTGGTTTC
         │ 23 TCAGATTAAATATATGGGAAATGCAAGTTAATTTGGATGCACATAAGGTGTTTGCTGAAATGTCTATGAGAAATGTTGTTTCTTGGACTTAGAATGATATACACTGTCGTCCTTTGGTTTC
         │ 24 TCAGATTAAATATATGGGAAATGCAAGTTAATTTGGATGCACATAAGGTGTTTGCTGAAATGTCTATGAGAAATGTTGTTTCTTGGACTTAGAATGATATACACTGTCGTCCTTTGGTTTC
         └ 25 TCAGATTAAATATATGGGAAATGCAAGTTAATTTGGATGCACATAAGGTGTTTGCTGAAATGTCTATGAGAAATGTTGTTTCTTGGACTTAGAATGATATACACTGTCGTCCTTTGGTTTC
```

SPINACH PLANT HAVING NOVEL DOWNY MILDEW RESISTANCE GENE

TECHNICAL FIELD

The present invention relates to a spinach plant having a gene that exhibits resistance to a broad range of races of downy mildew, and also relates to a method for producing the spinach plant.

CROSS REFERENCE TO RELATED APPLICATIONS

This application is a 35 U.S.C. § 371 United States National Phase Application which claims the benefit of, and priority to, PCT Application No. PCT/JP2022/040890, filed Nov. 1, 2022, which claims the benefit of, and priority to, Japanese Patent Application no. 2021-178897, filed Nov. 1, 2021. The entire contents of the aforementioned applications are incorporated by reference herein.

SEQUENCE LISTING

This application incorporates by reference in its entirety the Sequence Listing entitled "PC-35220.xml" (4 KB), which was created on Oct. 31, 2022, using the WIPO Sequence software package v. 2.2.0 and filed electronically herewith.

BACKGROUND ART

Spinach (*Spinacia oleracea* L.) is an annual or perennial plant belonging to the genus *Spinacia* of the family Amaranthaceae that is native to western Asia and widely cultivated. It is thought to have first been brought to Japan from China in the Edo period. Generally, the radical leaves (rosette) of spinach are used for food consumption, and because the levels of vitamins, iron and calcium in spinach are particularly high, the nutritional value is extremely high. In recent years, for reasons of nutrient level and convenience, the market for baby spinach leaves has grown rapidly, particularly in the Western world. Consequently, spinach is now one of the world's most important vegetables.

Plant varieties are generally either phenotypically uniform open pollinated lines or first filial generation hybrid (hereinafter abbreviated as "F1") varieties, and for most major crop species, F1 varieties are more prevalent. F1 varieties tend to exhibit more vigorous growth due to heterosis. As a result, F1 varieties offer considerable advantages, including rapid growth and increased yield, and can also be expected to exhibit improved environmental adaptability such as tolerance to pests and better tolerance to cold and extreme heat. Further, although being heterozygous, because individuals of an F1 variety possess the same genotype, the phenotype exhibits an extremely high degree of uniformity. Accordingly, the marketability of the product is enhanced. Moreover, because useful traits governed by dominant genes can be accumulated in the parent lines, faster breeding of desirable varieties is possible. Because of the type of superior characteristics described above, F1 varieties now represent the majority of cultivated species among the major crops. Similarly, in the case of spinach grown for food consumption, although phenotypically uniform open pollinated lines were predominant until the 1960s, rapid development of F1 varieties has occurred since the 1970s, and nowadays almost all cultivated spinach is F1 varieties.

One of the diseases that damages spinach is downy mildew, which is caused by the fungal pathogen *Peronospora effusa* (alternative name: *Peronospora farinosa* f. sp. *spinaciae*) (commonly abbreviated as Pfs). Downy mildew is one of the most serious spinach diseases, with damage spreading rapidly and having an extremely severe effect on the product yield and quality. Countermeasures that have been attempted for downy mildew include control of the pathogenic organism, either by cultural control or chemical control using agricultural chemicals or the like, but the use of resistant varieties has proven the most effective method in terms of environmental impact, cultivation labor, and cost and the like.

Downy mildew is known to exhibit rapid development of new pathogenic races, with such new races being able to evade or overcome heritable resistance traits of varieties that were previously resistant to all known races. The International Working Group on *Peronospora* in spinach (IWGP) is a consortium of seed companies that have received research support from the University of Arkansas and the University of California (USA) and the Netherlands Inspection Service for Horticulture (Naktuinbouw). The IWGP monitors the appearance and spread of new races of downy mildew, and assigns formal names to those races. Since the first report of a downy mildew outbreak in 1824, 19 races of downy mildew have been named to date (Non-Patent Document 1).

To adapt to this continual appearance of new races, the search for novel resistant materials is extremely important in the breeding of spinach. The search for downy mildew resistant genetic material is occurring not only among cultivated species, but also within wild species. For example, according to the Center for Genetic Resources, the Netherlands (CGN), searches for downy mildew resistance genetic material were conducted in 2008 within the wild species of spinach *Spinacia turkestanica*, and in 2011 within the wild species of spinach *Spinacia tetrandra*. Further, in 2011, Correll et al. reported that six types of RPF genes controlled known downy mildew resistance (Non-Patent Document 2). Moreover, RPF1 to RPF10, RPF11 (Patent Document 1), RPF12 (Patent Document 2), RPF13 (Patent Document 3), RPF14 (Patent Document 4), RPF15 (Patent Document 5), R6 (Patent Document 6), and R15 (Patent Document 7) and the like have all been reported as downy mildew resistance genes. By introducing a downy mildew resistance gene derived from a wild species of spinach into the cultivated spinach species *Spinacia oleracea* L., a spinach having superior downy mildew resistance can be developed (Patent Document 8).

RPF genes are a plurality of alleles, or a plurality of tightly linked genes, that exist at one gene locus known as the RPF gene locus. In an F1 variety, by incorporating two RPF alleles, broad resistance has been achieved (Non-Patent Document 3, Patent Document 5). For example, the RPF1 gene, the RPF2 gene and the RPF3 gene are located on chromosome 3 (Non-Patent Document 3), and the RPF15 gene is also located on chromosome 3 (Patent Document 5). Further, a downy mildew resistance gene disclosed in Patent Document 8 is stated to be located on linkage group 6, but according to sequence information, it is actually located on chromosome 3 (Patent Document 5).

A single WOLF gene or two WOLF genes, each of which is broadly classified as either an alpha WOLF gene or a beta WOLF gene depending on the structure, exist adjacently at the downy mildew resistance locus (Patent Document 9).

The alpha WOLF gene and the beta WOLF gene each include a plurality of alleles that impart a specific resistance profile, and the LRR domain sequence of each WOLF gene and the resistance pattern of each gene against various downy mildew races have been disclosed.

In theory, combining WOLF genes having different resistance patterns should enable the design of a desired resistance pattern. However, with conventional cross breeding, arbitrarily combining extremely tightly linked genes is practically impossible.

Moreover, variants that impart the desired resistance pattern can also be developed by introducing a downy mildew resistance gene from externally by genetic transformation (GMO), or by endogenous gene editing. However, crops developed by GMO or gene editing suffer from the problem of being still not widely accepted by the general public.

The downy mildew resistance gene p10 is located on chromosome 1, and has been reported to exhibit resistance to Pfs1, Pfs2, Pfs3, Pfs4, Pfs5, Pfs6, Pfs7, Pfs8, Pfs9, Pfs10, Pfs11, Pfs12, Pfs13, Pfs14, Pfs15 and Pfs16. However, the resistance imparted by the p10 gene is only expressed in the case of homozygosis, and the degree of resistance is only moderate (Patent Document 10). As a result, it is surmised that breeding resistant varieties using the p10 gene is not only more difficult than breeding varieties that use genes having dominant resistance expression, but also results in a degree of tolerance that cannot be claimed to be entirely satisfactory from a practical perspective. Furthermore, the *Spinacia tetrandra* line CGN120251 has a downy mildew resistance gene located on chromosome 4, and has been reported to exhibit resistance to Pfs4, Pfs7, Pfs9, Pfs10, Pfs11, Pfs12, Pfs13, Pfs14, Pfs15, Pfs16 and Pfs17 (Patent Document 11).

Among commercially available spinach varieties, although some phenotypically uniform open pollinated lines do exist, almost all varieties are hybrids using female lines and male lines. Male and female parents typically have mutually different resistance genes. For example, the hybrid variety '*Andromeda*' (developed by Nunhems B.V.) exhibits resistance to Pfs1 through Pfs12 and Pfs14. The resistance to Pfs1, 3, 5, 8, 9, 11, 12 and 14 is imparted by the resistance genes of one parent, and the resistance to Pfs1 through 10 is imparted by the resistance genes of the other parent (Patent Document 4).

CITATION LIST

Patent Documents

[Patent Document 1]
U.S. Pat. No. 10,258,001
[Patent Document 2]
U.S. Pat. No. 10,258,002
[Patent Document 3]
International Patent Publication No. WO2015/036378
[Patent Document 4]
International Patent Publication No. WO2019/145446
[Patent Document 5]
International Patent Publication No. WO2019/145447
[Patent Document 6]
Japanese Patent (Granted) Publication No. 6457269
[Patent Document 7]
U.S. Pat. No. 9,974,276
[Patent Document 8]
Japanese Patent (Granted) Publication No. 6684207
[Patent Document 9]
International Patent Publication No. WO2018/059651
[Patent Document 10]
U.S. Patent Application No. 2019/0104700
[Patent Document 11]
International Patent Publication No. WO2020/239215

Non Patent Documents

[Non Patent Document 1]
Plantum, "Denomination of Pe: 18 and 19, two new races of downy mildew in spinach", [online], Apr. 15, 2021, [search: Oct. 4, 2021]
[Non Patent Document 2]
Correll et al., European Journal of Plant Pathology, 2011, vol. 129, pp. 193-205.
[Non Patent Document 3]
Feng et. al, Euphytica, 2018, 214:174.
[Non Patent Document 4]
International Seed Federation, "Differential Sets *Peronospora farinosa* f. sp. *spinaciae* (*P. effusa*)", 2018
[Non Patent Document 5]
Iwata and Ninomiya, Breeding Science, 2006, vol. 56 (4), pp. 371-377.

SUMMARY OF INVENTION

Problems to be Solved by the Invention

At present, there is no single resistance gene that is known to impart resistance to all named Pfs races (Pfs1 to Pfs 19) and the types UA1014, Be2105B and PV2144. Consequently, in order to achieve resistance to all currently known Pfs races using known resistance genes, multiple resistance genes must be combined.

Accordingly, the present invention has an object of providing a single dominant downy mildew resistance gene that imparts resistance to at least all of Pfs1 to Pfs19, and types UA1014, Be2105B and PV2144.

Means for Solving the Problems

As a result of intensive research conducted in order to achieve the above object, the inventors of the present invention discovered that a novel dominant downy mildew resistance gene that exhibits resistance at least all of Pfs1 to Pfs19, and types UA1014, Be2105B and PV2144 exists on chromosome 3 of the *Spinacia tetrandra* line RNR140003, and we named this gene the RPF-SK1 gene. Moreover, the inventors also discovered that by conducting interspecific crossing between a wild species of spinach having this downy mildew resistance gene and a cultivated species of spinach to obtain an F1 individual having downy mildew resistance, and then repeating crossing of this F1 individual with a cultivated species of spinach, a spinach plant having the downy mildew resistance attributable to the wild species' downy mildew resistance gene, and having characteristics similar to the cultivated species could be developed, enabling them to complete the present invention.

In other words, the present invention is as described below.

[1] A downy mildew resistant spinach plant having a downy mildew resistance RPF-SK1 gene in at least one allele, wherein
in the RPF-SK1 gene:
(a) a SNP identified by chr3_1215815 is cytosine,
(b) a SNP identified by chr3_1215855 is thymine, (c) a SNP identified by chr3_1216014 is cytosine, (d) a SNP identified by chr3_1216093 is guanine, a SNP identified by chr3_1216094 is guanine, and a SNP identified by chr3_1216095 is adenine, (e) a SNP identified by chr3_1216288 is adenine, or (f) a SNP identified by chr3_1216291 is guanine.

[2] The downy mildew resistant spinach plant according to [1] above, wherein the RPF-SK1 gene is either homozygous or heterozygous.

[3] The downy mildew resistant spinach plant according to [1] or [2] above, wherein the plant is resistant to at least downy mildew races Pfs1, Pfs2, Pfs3, Pfs4, Pfs5, Pfs6, Pfs7, Pfs8, Pfs9, Pfs10, Pfs11, Pfs12, Pfs13, Pfs14, Pfs15, Pfs16, Pfs17, Pfs18, Pfs19 and UA1014 type, and also resistant to a race indicated by UA1014 type.

[4] The downy mildew resistant spinach plant according to any one of [1] to [3] above, wherein the plant is resistant to at least downy mildew races indicated by Be2105B type and PV2144 type.

[5] The downy mildew resistant spinach plant according to any one of [1] to [4] above, wherein the downy mildew resistant spinach plant is derived from an interspecific hybrid plant of *Spinacia tetrandra* and a cultivated species of spinach.

[6] The downy mildew resistant spinach plant according to any one of [1] to [5] above, having downy mildew resistance derived from a plant specified in accession number FERM BP-22426.

[7] The downy mildew resistant spinach plant according to any one of [1] to [6] above, having at least one type of downy mildew resistance gene besides the RPF-SK1 gene.

[8] A downy mildew resistant spinach plant that is a downy mildew resistant spinach plant specified in accession number FERM BP-22426, a hybrid plant obtained using the downy mildew resistant spinach plant as a parent, or a progeny of either of these plants.

[9] A method for predicting downy mildew resistance of a spinach plant, the method comprising investigating genotypes of at least one SNP selected from the group consisting of chr3_1215815, chr3_1215855, chr3_1216014, chr3_1216093, chr3_1216094, chr3_1216095, chr3_1216288 and chr3_1216291 of a test spinach plant, and predicting that the test spinach plant will have a high probability of exhibiting downy mildew resistance in those cases where, in at least one allele:

(a) a SNP identified by chr3_1215815 is cytosine, (b) a SNP identified by chr3_1215855 is thymine, (c) a SNP identified by chr3_1216014 is cytosine, (d) a SNP identified by chr3_1216093 is guanine, a SNP identified by chr3_1216094 is guanine, and a SNP identified by chr3_1216095 is adenine, (e) a SNP identified by chr3_1216288 is adenine, or (f) a SNP identified by chr3_1216291 is guanine.

[10] A method for screening downy mildew resistant spinach plants, the method comprising investigating genotypes of at least one SNP selected from the group consisting of chr3_1215815, chr3_1215855, chr3_1216014, chr3_1216093, chr3_1216094, chr3_1216095, chr3_1216288 and chr3_1216291 of a test spinach plant, and selecting the test spinach plant as a downy mildew resistant spinach plant in those cases where, in at least one allele:

(a) a SNP identified by chr3_1215815 is cytosine, (b) a SNP identified by chr3_1215855 is thymine, (c) a SNP identified by chr3_1216014 is cytosine, (d) a SNP identified by chr3_1216093 is guanine, a SNP identified by chr3_1216094 is guanine, and a SNP identified by chr3_1216095 is adenine, (e) a SNP identified by chr3_1216288 is adenine, or (f) a SNP identified by chr3_1216291 is guanine.

[11] A method for producing a downy mildew resistant spinach plant, the method having:

a first crossing step of crossing a spinach plant having an RPF-SK1 gene and an arbitrary spinach plant, a second crossing step of obtaining a segregating population by subjecting an F1 individual obtained in the first crossing step to self-pollination, back-crossing, or interspecific crossing or intraspecific crossing with a spinach plant different from the parent used in the first crossing step, and a selection step of selecting a spinach plant having an RPF-SK1 gene from the segregating population.

[12] The method for producing a downy mildew resistant spinach plant according to [11] above, wherein the arbitrary spinach plant, or the parent used in the interspecific crossing or intraspecific crossing in the second crossing step is a spinach plant having at least one type of downy mildew resistance gene besides the RPF-SK1 gene.

[13] A portion of a plant body of the downy mildew resistant spinach plant according to any one of [1] to [8] above.

[14] A leaf of the downy mildew resistant spinach plant according to any one of [1] to [8] above.

[15] A seed of the downy mildew resistant spinach plant according to any one of [1] to [8] above.

[16] A kit which is used for selecting a spinach plant having an RPF-SK1 gene, the kit comprising:

a forward primer and a reverse primer for conducting PCR amplification of a region including chr3_1215815 to chr3_1216291 of a test spinach plant.

Effects of the Invention

According to the present invention, a downy mildew resistant spinach plant that exhibits resistance to a broad range of races can be provided.

Further, by using the spinach plant according to the present invention as a parent, a novel spinach line that exhibits resistance to a broad range of races can be developed.

BRIEF DESCRIPTION OF DRAWINGS

FIG. 1D is an alignment map in the vicinity of the RPF-SK1 gene locus of chromosome 3 (chr3_1216377 to chr3_1216498) of a spinach.

DESCRIPTION OF EMBODIMENTS

Figure 1A:
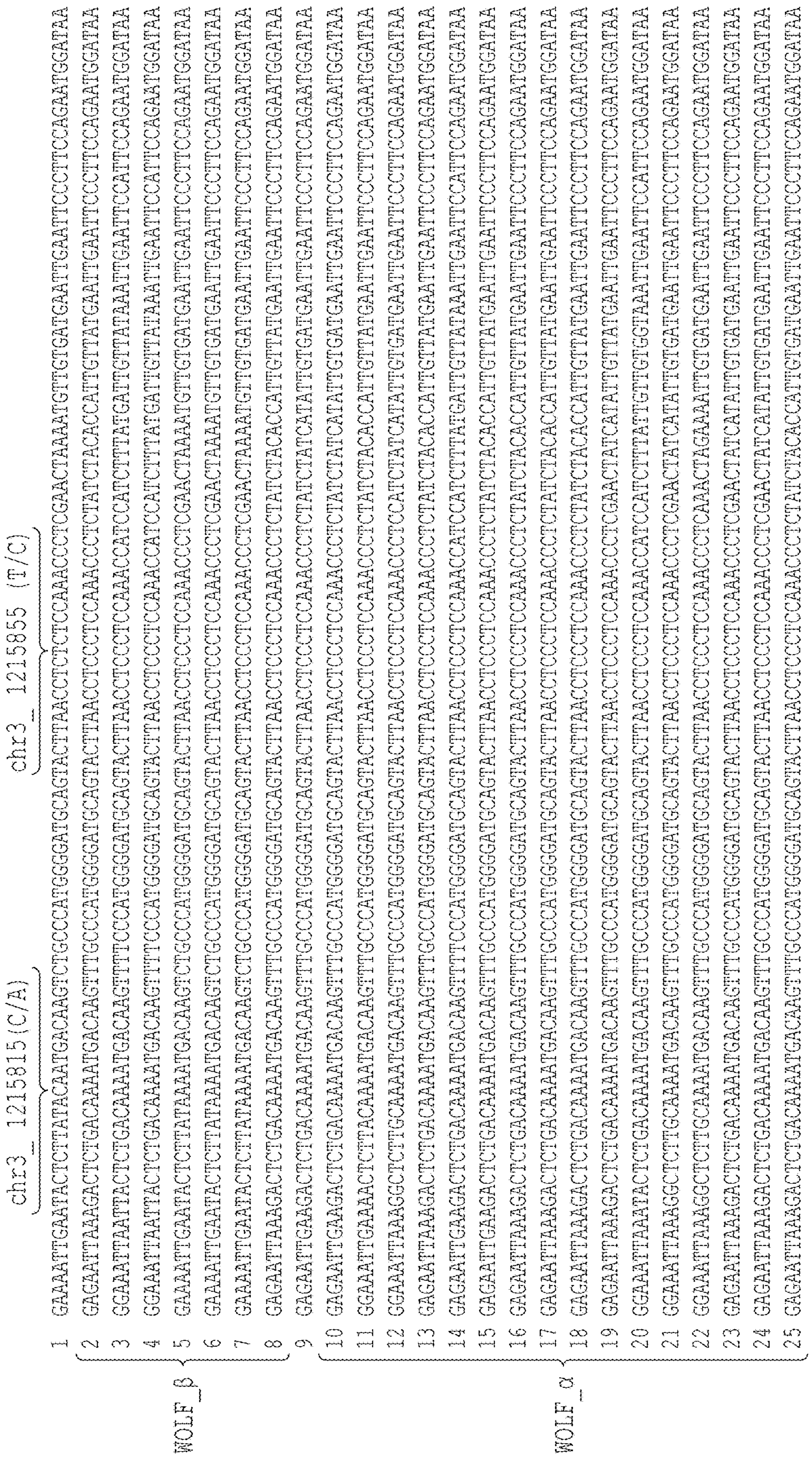
FIG. 1A is an alignment map in the vicinity of the RPF-SK1 gene locus of chromosome 3 (chr3_1215795 to chr3_1215913) of a spinach.

In the present invention and the present description, a spinach plant describes a plant that is classified as belonging to the genus *Spinacia*. Examples of wild species of spinach include *Spinacia tetrandra* and *Spinacia turkestanica* and the like. Further, examples of cultivated species of spinach include *Spinacia oleracea* L. and the like. In the present invention and the present description, these "cultivated species" describe plants of varieties used in cultivation, and include not only phenotypically uniform open pollinated lines, but also F1 varieties.

In the present invention and the present description, downy mildew describes a disease caused by a pathogen belonging to the family Peronosporaceae. The main pathogenic organisms responsible for spinach downy mildew are denoted Pfs (*Peronospora farinosa* f. sp. *spinaciae*), and currently, races Pfs1 to Pfs19 have been numbered. In addition to these races, many unnumbered races also exist, such as the races that exhibit pathogenicity of the UA1014, Be2105B and PV2144 types.

In the present invention and the present description, the terminology "chrX_Y" (wherein X and Y are integers) of a spinach plant means the nucleotide base, within the genome of the spinach plant, which corresponds with base Y of chromosome X (also called the Xth chromosome) in the reference genome (Spinach genome sequence (v1)) published in SpinachBase. The "nucleotide base corresponding with base Y of chromosome X in the SpinachBase reference genome" in any particular spinach plant can be determined by aligning the nucleotide sequence of the genomic DNA of the spinach plant with the nucleotide sequence of the SpinachBase reference genome so as to achieve the highest degree of homology (sequence identity).

Accordingly, the chromosome X of any particular spinach plant can be indicated as the chromosome X of the spinach plant determined by aligning the nucleotide sequence of the genomic DNA of the spinach plant with the nucleotide sequence of the SpinachBase reference genome so as to achieve the highest degree of homology (sequence identity).

In the present invention and the present description, the term "chromosome" includes not only the entire chromosome, but also portions thereof. In other words "a portion of a chromosome" may sometimes simply be referred to as "a chromosome".

An "X gene locus" is a "site occupied by the X gene in the chromosome". Accordingly, in the present invention and the present description, a "spinach plant having an X gene locus" is a spinach plant having a site occupied by the X gene within the chromosome and has the same meaning as a "spinach plant having an X gene".

In the present invention and the present description, a "production method" can also be called a "development method" or a "breeding method". In other words, the terms "production", "development" and "breeding" may all be used with the same meaning.

In the present invention and the present description, the expression "portion of the plant body" includes the cells and tissues of the plant body, and specific examples include the leaves, seeds, flowers, stems, roots, and fruit and the like. In addition, protoplasts obtained from cells of the plant body are also included.

<Downy Mildew Resistant Spinach Plant>

The downy mildew resistant spinach plant according to the present invention is a spinach plant, other than *Spinacia tetrandra*, having an RPF-SK1 gene which is a downy mildew resistance gene located on the RPF gene locus of the wild species of spinach known as *Spinacia tetrandra* line RNR140003. The RPF-SK1 gene has one of the following SNPs within the RPF gene of the spinach plant:

(a) the SNP identified by chr3_1215815 is cytosine,
(b) the SNP identified by chr3_1215855 is thymine,
(c) the SNP identified by chr3_1216014 is cytosine,
(d) the SNP identified by chr3_1216093 is guanine, the SNP identified by chr3_1216094 is guanine, and the SNP identified by chr3_1216095 is adenine,
(e) the SNP identified by chr3_1216288 is adenine, or
(f) the SNP identified by chr3_1216291 is guanine.

The RPF-SK1 gene is a novel downy mildew resistance gene that imparts resistance to at least all of the downy mildew races Pfs1 through Pfs 19, and the races indicated by UA1014, Be2105B and PV2144 types. Although a variety of RPF genes have already been reported as downy mildew resistance genes, in order to achieve resistance to a broad range of races, these RPF genes have required the use of multiple RPF alleles. The RPF-SK1 gene can, with a single allele, impart resistance to all of the downy mildew races Pfs1 through Pfs19, and the UA1014, Be2105B and PV2144 types, and is therefore a particularly superior downy mildew resistance gene with resistance not seen conventionally, making it extremely useful in the development of a downy mildew resistant spinach.

The RPF-SK1 gene is a gene that is dominantly inherited by progeny. As a result, a spinach plant according to the present invention may be a spinach plant in which the RPF-SK1 gene is homozygous, namely a spinach plant having a homozygous RPF-SK1 gene, or a spinach plant having a heterozygous RPF-SK1 gene. Because a spinach plant according to the present invention has the RPF-SK1 gene, which is a single dominant downy mildew resistance gene which alone is capable of imparting resistance to an extremely broad range of downy mildew races, said spinach plant exhibits excellent performance as a downy mildew resistant spinach.

The downy mildew resistant spinach plant according to the present invention can be developed by introducing the RPF-SK1 gene into the genomic DNA of a spinach plant other than *Spinacia tetrandra*. This introduction of the RPF-SK1 gene into the genomic DNA can be achieved, for example, by introducing a chromosome fragment that includes the site where the RPF-SK1 gene is located (the RPF-SK1 gene locus) in the *Spinacia tetrandra* line RNR140003. There are no limitations on the site within the chromosome into which the chromosome fragment including the RPF-SK1 gene locus is introduced, and an extrachromosomal site is also possible. For example, the downy mildew resistant spinach plant according to the present invention includes spinach plants in which a chromosome fragment including the RPF-SK1 gene locus has been used to substitute a region within chromosome 3 that corresponds with that fragment, as well as spinach plants in which a chromosome fragment including the RPF-SK1 gene locus has been introduced by translocation or the like into a region other than a region corresponding with the RPF-SK1 gene locus within chromosome 3 of *Spinacia tetrandra*. Examples of the chromosome fragment including the RPF-SK1 gene locus include the nucleotide shown in SEQ ID NO: 3, 4 and 5, and Table 1.

Introduction of the RPF-SK1 gene into the genomic DNA may be conducted by cross breeding methods using *Spinacia tetrandra* as a parent, or by genetic modification methods such as genome editing.

For example, the downy mildew resistant spinach plant according to the present invention may be a plant derived from an interspecific hybrid plant of *Spinacia tetrandra* and a spinach plant other than *Spinacia tetrandra*, wherein the plant has downy mildew resistance derived from the RPF-SK1 gene. The term “interspecific hybrid plant” includes plants produced by crossing of different species of plants belonging to the genus *Spinacia*, as well as somatic cell hybrid plants produced by interspecific cell fusion of plants of the genus *Spinacia*, and grafted hybrid plants obtained by interspecific grafting of plants of the genus *Spinacia*. Further, the expression “interspecific hybrid plant of *Spinacia tetrandra* and a spinach plant other than *Spinacia tetrandra*” includes not only the interspecific hybrid plants mentioned above, but also the progeny of those interspecific hybrid plants.

In the present invention and the present description, the expression “progeny of a spinach plant” includes descendants obtained by intraspecific crossing of the spinach plant, as well as individuals obtained with the spinach plant as a parent and the descendants thereof, somatic cell hybrid plants obtained by cell fusion of cells of the spinach plant and cells of a plant of a different variety and the descendants thereof, and individuals obtained by grafting using the spinach plant as either the stock or the scion and the descendants thereof. The term “descendants” includes both individuals obtained by intraspecific crossing and individuals obtained by interspecific crossing. Further, the expression “individuals obtained with the plant as a parent” means individuals obtained by intraspecific crossing, interspecific crossing, cell fusion or grafting, with the plant acting as a parent.

For example, the downy mildew resistant spinach plant according to the present invention may be developed by crossing *Spinacia tetrandra* and a spinach plant other than *Spinacia tetrandra*. In an F1 individual obtained by interspecific crossing with *Spinacia tetrandra* as a parent, at least one allele has the RPF-SK1 gene derived from *Spinacia tetrandra*. Because the RPF-SK1 gene is a dominant gene, F1 individuals having a chromosome 3 derived from *Spinacia tetrandra* will have downy mildew resistance derived from the RPF-SK1 gene.

There are no limitations on the spinach plant used as material in developing the downy mildew resistant spinach plant according to the present invention, and any spinach plant having the RPF-SK1 gene found in the *Spinacia tetrandra* line RNR140003 may be used. Examples of the *Spinacia tetrandra* line other than RNR140003 include progeny lines that have inherited the RPF-SK1 gene from RNR140003.

There are no limitations on the parent crossed with *Spinacia tetrandra* in order to develop the downy mildew resistant spinach plant according to the present invention, provided the parent is a spinach plant other than *Spinacia tetrandra*, but a cultivated species of spinach plant that is cultivated as a crop is preferred. *Spinacia tetrandra* is a wild species, and in terms of use as a crop, characteristics such as the germination properties, pollen quality, leaf color and leaf shape are inferior to the cultivated species of spinach. By using a cultivated species of spinach as the parent for crossing with *Spinacia tetrandra*, the characteristics of the resulting downy mildew resistant spinach plant, other than the downy mildew resistance, approach more preferred characteristics for an agricultural crop. Examples of cultivated species of spinach plants include *Spinacia oleracea* L., and interspecific hybrid spinach plants developed using *Spinacia oleracea* L. as a parent.

The downy mildew resistant spinach plant according to the present invention may also be a progeny of an F1 individual obtained by interspecific crossing of *Spinacia tetrandra* and a spinach plant other than *Spinacia tetrandra*. For example, an F1 seed is obtained by crossing *Spinacia tetrandra* and a cultivated species of spinach plant, and a plant obtained by growing the obtained F1 seed is then subjected to either self-pollination or backcrossing with an individual of a cultivated species of spinach plant to obtain seeds. Subsequently, an individual having the RPF-SK1 gene is selected from plants obtained by growing the obtained seeds. By repeating the process of subjecting the selected plant individual to self-pollination or crossing with a cultivated species of spinach plant, and then selecting an individual having the RPF-SK1 gene from the progeny obtained upon crossing, a phenotypically uniform open pollinated variety of downy mildew resistant spinach plant can be obtained. The self-pollination, crossing with a cultivated species of spinach plant, cultivation and seed production may be conducted using typical methods employed in spinach cultivation.

Selection of an individual having the RPF-SK1 gene from progeny obtained by crossing can be achieved, for example, by investigating the downy mildew resistance. Specifically, Pfs of each of the various races may be used to separately inoculate the leaves of a test plant for which downy mildew resistance is to be investigated, and observation then made as to whether or not the disease develops. If a symptom of downy mildew does not develop, that test plant may be evaluated as having resistance to the inoculated race. A plant from among the progeny obtained by crossing that exhibits resistance to at least all of the downy mildew races Pfs1 through Pfs19, and the races indicated by UA1014, Be2105B and PV2144 types may then be selected as an individual having the RPF-SK1 gene.

Selection of an individual having the RPF-SK1 gene from progeny obtained by crossing can also be achieved, for example, by using a method for investigating whether the genomic DNA includes a chromosome fragment that includes the RPF-SK1 gene. Specifically, identification can be made by using a DNA marker within the RPF-SK1 gene locus of the spinach plant.

In the present invention and the present description, a DNA marker is a marker that can detect differences in DNA sequences on chromosomes to discriminate between chromosome fragments derived from different varieties or lines. Examples of DNA markers include SNP (Single Nucleotide Polymorphism) markers, SSR (Simple Sequence Repeats) markers and RFLP (Restriction Fragment Length Polymorphism) markers.

DNA marker detection can be achieved using typical methods. For example, using DNA extracted from each plant individual as a template, a nucleotide amplification reaction may be conducted using a polymerase and a primer capable of hybridizing specifically with a specific SNP or SSR, and an electrophoresis method or the like then used to detect the presence or absence of an amplification product, thus enabling identification of each polymorphism. Alternatively, DNA extracted from each plant individual may be subjected to a restriction enzyme treatment, and an electrophoresis method or the like then used to detect the DNA fragment pattern, thus enabling identification of each polymorphism. Primers capable of hybridizing specifically with a specific SNP or SSR can be designed by typical methods using widely used primer design tools, in accordance with the nucleotide sequence of the genomic DNA of the spinach, and the nucleotide sequence of the SNP or SSR that represents the detection target, and can then be synthesized using methods well known in the technical field.

Examples of DNA markers used in the selection of individuals having the RPF-SK1 gene include SNPs of chr3_1215815, chr3_1215855, chr3_1216014, chr3_1216093, chr3_1216094, chr3_1216095, chr3_1216288, and chr3_1216291. However, chr3_1216093, chr3_1216094 and chr3_1216095 represent a sequence of three nucleotides specific to the RPF-SK1 gene, and this combination of three SNPs acts as a DNA marker that can be used in the selection of individuals having the RPF-SK1 gene. For these SNPs, the genotype of the RPF-SK1 gene and the genotype of the reference genome published in SpinachBase are shown in Table 1. In Table 1, G means guanine, C means cytosine, A means adenine, and T means thymine.

TABLE 1

| SNP | Genotype of RPF-SK1 gene | Genotype of reference genome |
|---|---|---|
| chr3_1215815 | C | A |
| chr3_1215855 | T | C |
| chr3_1216014 | C | G |
| chr3_1216093, chr3_1216094, chr3_1216095 | GGA | GGC |
| chr3_1216288 | A | G |
| chr3_1216291 | G | T |

Identification of the nucleotides of these SNPs can be made, for example, using Kompetitive Allele Specific PCR (KASP) genotyping assay (manufactured by LGC Genomics GmbH). Further, the nucleotides of these SNPs can also be identified by conducting a PCR amplification of a region including chr3_1215815 to chr3_1216291 using genomic DNA extracted from a test spinach plant as a template, and then identifying the nucleotide sequence of the obtained amplification product.

For example, among downy mildew resistant spinach plants according to the present invention, spinach plants having a fragment that includes the RPF-SK1 gene locus of the *Spinacia tetrandra* line RNR140003 either homozygously or heterozygously have at least one allele in which the SNP identified by chr3_1215815 is cytosine, the SNP identified by chr3_1215855 is thymine, the SNP identified by chr3_1216014 is cytosine, the three consecutive SNPs identified by chr3_1216093 to chr3_1216095 are guanine-guanine-adenine, the SNP identified by chr3_1216288 is adenine, and the SNP identified by chr3_1216291 is guanine.

The downy mildew resistant spinach plant according to the present invention preferably has characteristics other than the downy mildew resistance, and particularly characteristics as a crop, that are either the same as, or similar to, cultivated species of spinach. Examples of these characteristics as a crop include taste, leaf shape, yield, and ease of cultivation and the like. The expression "characteristics as a cultivated species" means that the characteristics as a crop are characteristics that are suited to use of the plant as an agricultural crop.

The downy mildew resistant spinach plant according to the present invention preferably also has at least one type of downy mildew resistance gene besides the RPF-SK1 gene. The RPF-SK1 gene can alone impart resistance to a broader range of races than any known resistance gene, but also incorporating another downy mildew resistance gene can be expected to contribute to suppressing the appearance of new races that may break through this resistance. Although there are no limitations on the downy mildew resistance gene besides the RPF-SK1 gene, in the case of heterozygotes, examples include the RPF1 gene to RPF15 gene, the R6 gene, and the R15 gene and the like.

The downy mildew resistant spinach plant according to the present invention may be either the entirety or a portion of the plant body. In other words, the downy mildew resistant spinach plant according to the present invention includes the entire plant body of the spinach plant having the RPF-SK1 gene, the above ground portion of the spinach plant, and the tissues of the spinach plant. Further, the downy mildew resistant spinach plant according to the present invention also includes cells obtained from any tissue of the spinach plant having the RPF-SK1 gene. Examples of this tissue include the embryo, meristem cells, callus, pollen, leaves, anthers, stem, petioles, roots, root apices, fruit, seeds, flowers, cotyledons, and hypocotyl and the like.

Further, cells harvested from the tissues of the downy mildew resistant spinach plant according to the present invention are also useful. These cells have the genomic DNA of the spinach plant and are plant cells having the RPF-SK1 gene. The spinach plant cell having the RPF-SK1 gene may be either a single cell, or a cell cluster composed of a plurality of cells. The spinach plant cells having the RPF-SK1 gene may be harvested from any of the tissues of the spinach plant, or may be a cell mixture containing a mixture of cells harvested from different tissues. Examples of these tissues include the same tissues as those described above. Among these possibilities, single cells derived from the tissue of leaf blades or petioles are preferred.

The downy mildew resistance of the downy mildew resistant spinach plant according to the present invention exhibits dominant expression. As a result, by conducting interspecific crossing or intraspecific crossing using the downy mildew resistant spinach plant according to the present invention as a parent, novel lines of spinach plants having downy mildew resistance derived from the RPF-SK1 gene can be developed.

<Method for Screening Downy Mildew Resistant Spinach Plants>

A method for screening downy mildew resistant spinach plants according to the present invention includes investigating whether a test spinach plant has the RPF-SK1 gene, and then selecting the test spinach plant as a downy mildew resistant spinach plant in those cases where the test plant is determined as having the RPF-SK1 gene. In the method for screening downy mildew resistant spinach plants according to the present invention, the determination as to whether the test spinach plant has the RPF-SK1 gene can be made on the basis of the genotype of a DNA marker for the RPF-SK1 gene locus or a region within the vicinity thereof, or the genotype of a DNA marker strongly linked with these DNA markers. In those cases where, in at least one allele, the genotype of a DNA marker for the RPF-SK1 gene locus or a region within the vicinity thereof or a DNA marker strongly linked with these DNA markers has the same genotype as that of a *Spinacia tetrandra* such as RNR140003 which has an RPF-SK1 gene and exhibits downy mildew resistance, the test spinach plant may be selected as a downy mildew resistant spinach plant.

Examples of DNA markers that can be used for determining the presence or absence of the RPF-SK1 gene include the SNPs shown in Table 1. Among these, at least one SNP from the spinach plant selected from the group consisting of the SNP identified by chr3_1215815, the SNP identified by chr3_1215855, the SNP identified by chr3_1216014, the SNP identified by chr3_1216093, the SNP identified by chr3_1216094, the SNP identified by chr3_1216095, the SNP identified by chr3_1216288, the SNP identified by chr3_1216291, and SNPs genetically strongly linked to these SNPs is ideal as the DNA marker for determining the presence or absence of the RPF-SK1 gene. For example, in those cases where, in at least one allele, (a) the SNP identified by chr3_1215815 is cytosine, (b) the SNP identified by chr3_1215855 is thymine, (c) the SNP identified by chr3_1216014 is cytosine, (d) the SNP identified by chr3_1216093 is guanine, the SNP identified by chr3_1216094 is guanine, and the SNP identified by chr3_1216095 is adenine, (e) the SNP identified by chr3_1216288 is adenine, or (f) the SNP identified by chr3_1216291 is guanine, the test spinach plant may be selected as a downy mildew resistant spinach plant.

By preparing a kit form of a primer set for identifying the genotype of a DNA marker used for determining the presence or absence of the RPF-SK1 gene, and then using that kit, the determination of the presence or absence of the RPF-SK1 gene, and subsequent selection of downy mildew resistant spinach plants can be performed more easily. For example, a forward primer and reverse primer for conducting PCR amplification of a region including chr3_1215815 to chr3_1216291 from within the genomic DNA of the spinach plant may be included in a kit for selecting spinach plants having the RPF-SK1 gene. Further, a kit combining a primer set for identifying the genotype of the SNP identified by chr3_1215815, a primer set for identifying the genotype of the SNP identified by chr3_1215855, a primer set for identifying the genotype of the SNP identified by chr3_1216014, a primer set for identifying the genotypes of the three consecutive SNPs identified by chr3_1216093, chr3_1216094 and chr3_1216095, a primer set for identifying the genotype of the SNP identified by chr3_1216288, or a primer set for identifying the genotype of the SNP identified by chr3_1216291 is useful for identifying the genotypes of these SNPs to enable determination of the presence or absence of the RPF-SK1 gene in a test spinach plant.

<Method for Predicting Downy Mildew Resistance of Spinach Plants>

A method for predicting the downy mildew resistance of a spinach plant according to the present invention includes investigating whether a test spinach plant has the RPF-SK1 gene, and in those cases where the test plant is determined as having the RPF-SK1 gene, predicting that the test spinach plant will have a high probability of exhibiting downy mildew resistance. In the method for predicting the downy mildew resistance of a spinach plant according to the present invention, the determination as to whether the test spinach plant has the RPF-SK1 gene can be made on the basis of the genotype of a DNA marker for the RPF-SK1 gene locus or a region within the vicinity thereof, or the genotype of a DNA marker strongly linked with these DNA markers. In those cases where, in at least one allele, the genotype of a DNA marker for the RPF-SK1 gene locus or a region within the vicinity thereof or a DNA marker strongly linked with these DNA markers has the same genotype as that of a *Spinacia tetrandra* such as RNR140003 which has an RPF-SK1 gene and exhibits downy mildew resistance, the test spinach plant may be determined as having the RPF-SK1 gene, whereas in those cases where the genotype differs from that of a *Spinacia tetrandra* such as RNR140003 which has an RPF-SK1 gene and exhibits downy mildew resistance, the test spinach plant may be determined as lacking the RPF-SK1 gene.

Examples of DNA markers that can be used for determining the presence or absence of the RPF-SK1 gene include the SNPs shown in Table 1. For example, in those cases where, in at least one allele, (a) the SNP identified by chr3_1215815 is cytosine, (b) the SNP identified by chr3_1215855 is thymine, (c) the SNP identified by chr3_1216014 is cytosine, (d) the SNP identified by chr3_1216093 is guanine, the SNP identified by chr3_1216094 is guanine, and the SNP identified by chr3_1216095 is adenine, (e) the SNP identified by chr3_1216288 is adenine, or (f) the SNP identified by chr3_1216291 is guanine, the test spinach plant may be predicted as having the RPF-SK1 gene and having a high probability of exhibiting downy mildew resistance. Primer sets and kits for identifying the genotypes of DNA markers used in determining the presence or absence of the RPF-SK1 gene may employ the same primer sets and kits as those described above.

<Method for Producing Downy Mildew Resistant Spinach Plant>

By conducting cross-pollination using a spinach plant having the RPF-SK1 gene as a material, downy mildew resistance derived from the RPF-SK1 gene can be introduced into a spinach plant not having the RPF-SK1 gene, thus producing a novel downy mildew resistant spinach plant. The RPF-SK1 gene, which is a single dominant resistance gene, can be easily introduced into an arbitrary line, meaning the breeding of spinach varieties can be accelerated. For example, by using a spinach plant having a homozygous RPF-SK1 gene as a parent, varieties having resistance to a broader range of races can be more easily developed. Furthermore, the RPF-SK1 gene can be combined with another single dominant resistant allele in a different gene locus from the RPF-SK1 gene locus in the same haplotype.

The method for producing a downy mildew resistant spinach plant according to the present invention is a method that utilizes cross breeding using a spinach plant having the RPF-SK1 gene as a parent. Specifically, the method has a first crossing step of crossing a spinach plant having the RPF-SK1 gene and an arbitrary spinach plant, a second crossing step of obtaining a segregating population by subjecting an F1 individual obtained in the first crossing step to self-pollination, backcrossing, or interspecific crossing or intraspecific crossing with a spinach plant different from the parent used in the first crossing step, and a selection step of selecting a spinach plant having the RPF-SK1 gene from the segregating population. The self-pollination, backcrossing, interspecific crossing, intraspecific crossing, spinach plant cultivation and seed production may be conducted using typical methods employed in spinach cultivation.

*Spinacia tetrandra* may be used as the spinach plant having the RPF-SK1 gene used as a parent in the first crossing step, and the downy mildew resistant spinach plant of the present invention described above may also be used. In the present invention, the spinach plant having the RPF-SK1 gene used as a parent is preferably a downy mildew resistant spinach plant that has the RPF-SK1 gene, and also combines the characteristics of a cultivated species.

There are no limitations on the arbitrary spinach plant used as a parent in the first crossing step, or the arbitrary spinach plant used as a parent for the interspecific crossing or intraspecific crossing in the second crossing step, and any appropriate type of spinach plant lacking the RPF-SK1 gene may be used. In the present invention, the use of a cultivated species of spinach plant as this parent is preferred. For example, by using a downy mildew resistant spinach plant having the RPF-SK1 gene while also combining the characteristics of a cultivated species, and a cultivated species of spinach plant lacking the RPF-SK1 gene as parents, conducting crossing of these two parents, and then subjecting an obtained F1 individual to self-pollination, backcrossing, or interspecific crossing or intraspecific crossing with a cultivated species of spinach plant different from the parent used in the first crossing step, a novel spinach line having downy mildew resistance derived from the RPF-SK1 gene as well as the favorable characteristics of a cultivated species can be developed comparatively easily.

The arbitrary spinach plant used as a parent in the first crossing step, and the arbitrary spinach plant used as a parent for the interspecific crossing or intraspecific crossing in the second crossing step are preferably spinach plants having at least one type of downy mildew resistance gene other than the RPF-SK1 gene, and are more preferably cultivated species of spinach plants having at least one type of downy mildew resistance gene other than the RPF-SK1 gene. By using a spinach plant having at least one type of downy mildew resistance gene other than the RPF-SK1 gene as a parent, a novel spinach line including both the RPF-SK1 gene and another downy mildew resistance gene can be developed comparatively easily.

In the selection step, the selection of a spinach plant having the RPF-SK1 gene from the segregating population may be conducted, for example, by inoculating the leaves of a test plant separately with Pfs of each of the various races, and investigating the downy mildew resistance. A plant individual from within the segregating population that exhibits resistance to at least all of the downy mildew races Pfs1 to Pfs19, and the races indicated by the UA1014, Be2105B and PV2144 types is then selected as an individual having the RPF-SK1 gene.

Selection of an individual having the RPF-SK1 gene in the selection step may be conducted using a DNA marker for the RPF-SK1 gene locus of the spinach plant or a region in the vicinity thereof. The DNA marker and the specific method used may be the same as those described above in relation to the screening method according to the present invention.

In those cases where a plant individual including both the RPF-SK1 gene and another downy mildew resistance gene is to be selected, a DNA marker capable of identifying the presence or absence of the other downy mildew resistance gene is used together with the DNA marker described above for selection of an individual having the RPF-SK1 gene. Examples of DNA markers that may be used for identifying the presence or absence of the other downy mildew resistance gene include SNPs that exist in the gene locus of the other downy mildew resistance gene or in the vicinity thereof.

Subsequently, by repeating self-pollination of seeds collected from a selected progeny individual, a downy mildew resistant spinach plant can be obtained which exhibits more stable characteristics, and a more stable germination rate, yield, and seed productivity and the like that enable cultivation as a crop. There are no limitations on the number of repetitions of the self-pollination process provided the number is one or more, but the number of repetitions may be 2 or 3, or greater than 3.

EXAMPLES

Next, the present invention is described in further detail using a series of examples, but the present invention is not limited to the following examples.

<Race Inoculation Test for Investigating Downy Mildew Resistance>

Pfs inoculation tests on spinach plants were conducted using the method described below.

Spinach seeds were sowed in a tray filled with a culture soil "Super Mix A" (manufactured by Sakata Seed Corporation), and then covered with another culture soil "Metro-Mix 350" (manufactured by Hyponex Japan Co., Ltd.). During sowing, seeds of a line that exhibits susceptibility to the inoculated race were also sown in each tray to provide a diseased control group. The tray was placed in a glasshouse for two weeks to raise the seedlings, and at the two-leaf stage, the seedlings were inoculated by spraying with a Pfs spore suspension ($5\times10^4$/mL). Following inoculation, the tray was immediately covered with a plastic cover, and monitored under conditions including a temperature of 15° C., humidity of 100% and 12-hour long days.

Seven to ten days after inoculation, once disease had been obviously confirmed in the control group, each individual was evaluated for resistance or susceptibility. Plants for which mycelia and spores had appeared on the cotyledons or true leaves, confirming disease, were evaluated as being susceptible to disease, whereas plants for which no disease could be confirmed on either the cotyledons or the true leaves were deemed resistant.

Each race of downy mildew was acquired from within Japan, from The University of Arkansas (Dr. Jim Correll) or from Naktuinbouw. Further, differentiation of each downy mildew race was conducted using known spinach varieties that exhibit different resistance patterns to the various races as differential sets. These differential sets used in differentiating resistance to each downy mildew race can be acquired from USDA (United States Department of Agriculture) and Naktuinbouw (Non-Patent Document 4).

The resistance characteristics reported for each of the various differential sets are shown in Table 2 and Table 3. In the tables, "–" means resistance, "(–)" means medium resistance, "+" means disease susceptibility, and "(+)" means that disease symptoms and spore formation were observed only on the cotyledons, with no symptoms observed on the true leaves. Further "*" that the resistance results differed for each test.

TABLE 2

| Differential | | Viroflay | NIL 5 | NIL 3 | NIL 4 | NIL 6 | NIL 1 |
|---|---|---|---|---|---|---|---|
| Race - Pfs: | 1 | + | − | − | − | − | − |
| | 2 | + | − | + | − | + | − |
| | 3 | + | + | − | − | − | − |
| | 4 | + | + | + | − | − | − |
| | 5 | + | + | − | + | − | − |
| | 6 | + | + | + | + | + | − |
| | 7 | + | + | + | + | − | − |
| | 8 | + | + | − | + | + | + |
| | 9 | + | + | − | + | + | − |
| | 10 | + | + | + | + | + | + |
| | 11 | + | + | − | + | − | − |
| | 12 | + | + | − | + | + | + |
| | 13 | + | + | + | + | (−) | − |
| | 14 | + | + | − | + | + | + |
| | 15 | + | + | + | − | − | − |
| | 16 | + | + | − | + | − | − |
| | 17 | + | + | + | + | + | + |
| | 18 | + | + | + | + | − | − |
| | 19 | + | + | − | + | + | + |
| | UA1014 type | + | + | + | + | + | + |

TABLE 3

| Differential | | NIL 2 | Whale | Pigeon | Calandonia | Meerkat | Hydrus |
|---|---|---|---|---|---|---|---|
| Race - Pfs: | 1 | − | − | − | − | − | − |
| | 2 | − | − | − | − | − | − |
| | 3 | − | − | − | − | − | − |
| | 4 | − | (−) | − | − | − | − |
| | 5 | − | − | − | − | − | − |
| | 6 | − | (−) | − | − | − | − |
| | 7 | − | (−) | − | − | − | − |
| | 8 | − | − | − | − | − | − |
| | 9 | − | − | − | − | − | − |
| | 10 | − | (−)/+ * | − | − | − | − |
| | 11 | + | − | − | − | − | − |
| | 12 | + | − | − | − | − | − |
| | 13 | + | + | − | − | − | − |
| | 14 | + | − | + | − | − | − |
| | 15 | − | (−)/+ * | − | + | − | − |
| | 16 | + | − | + | − | + | − |
| | 17 | + | + | + | + | (−) | − |
| | 18 | + | + | + | + | + | − |
| | 19 | + | + | + | − | + | + |
| | UA1014 type | + | + | (+) | (+) | (+) | −/(+) * |

Example 1

Using a wild species of the *Spinacia tetrandra* line RNR140003 acquired from CGN of Holland in 2015 and 2016 as a parent, a novel downy mildew resistant line was developed.

First, the *Spinacia tetrandra* line RNR140003 was sown, and the germinated individuals were inoculated with Pfs10. The results revealed that all individuals exhibited resistance.

Subsequently, these *Spinacia tetrandra* line RNR140003 individuals were crossed with the advanced parent line SDF of *Spinacia oleracea* L., and F1 seeds were obtained. An advanced parent line means a parent that is desirable as a parent for developing a line that exhibits favorable characteristics as a cultivated species. Next, 18 of the obtained F1 seeds were sown, and the germinated individuals were inoculated with Pfs10. The results revealed that all individuals exhibited resistance. Backcrossing was then conducted using these individuals for which resistance had been confirmed as the seed parent and SDF as the pollen parent, and F1BC1 seeds were obtained. When the obtained F1BC1 seeds were sown, and the raised individuals were inoculated with Pfs10, to which SDF exhibits no resistance, resistant individuals (R) and susceptible individuals (individuals which do not exhibit resistance) (S) were obtained in a ratio of R:S=7:4.

Backcrossing was conducted using those individuals among the F1BC1 individuals for which resistance had been confirmed as the seed parent and SDF as the pollen parent, and F1BC2 seeds were obtained. When the obtained F1BC2 seeds were sown, and the raised individuals were inoculated with Pfs10, the R:S ratio was 15:28.

Another backcrossing was then conducted using those individuals among the F1BC2 individuals for which resistance had been confirmed as the seed parent and SDF as the pollen parent, and F1BC3 seeds were obtained. When the obtained F1BC3 seeds were sown, and the raised individuals were inoculated with Pfs10, the R:S ratio was 28:38.

Those F1BC3 individuals for which resistance had been confirmed were subjected to self-pollination, and F1BC3S1 seeds were obtained. When the obtained F1BC3S1 seeds were sown, and the raised individuals were inoculated with Pfs10, the R:S ratio was 18:2.

Those individuals among the F1BC3S1 individuals for which resistance had been confirmed were subjected to self-pollination, and F1BC3S2 seeds were obtained. When the obtained F1BC3S2 seeds were sown, and the raised individuals were inoculated with Pfs10, the R:S ratio was 26:0, indicating that they were fixed in a resistant genotype. All of the individuals for which resistance to Pfs10 had been confirmed were inoculated with Pfs12, and the R:S ratio was 23:0, indicating that they were fixed in a resistant genotype. In other words, the F1BC3S2 individuals all exhibited resistance to both Pfs10 and Pfs12. This line was named SDF (RNR) and seed multiplication of this line was conducted.

In each step, selection was conducted not only based on disease resistance, but also with due consideration of other factors such as the leaf color, leaf shape and leaf size, and as far as possible, those individuals having characteristics close to cultivated varieties were selected.

For the SDF (RNR) line, the applicants deposited seeds of this line in the National Institute of Technology and Evaluation (NITE) International Patent Organism Depositary (Room 120, 2-5-8 Kazusakamatari, Kisarazu-shi, Chiba, Japan). The identification code appended to the SDF (RNR) line by the depositor is SSC-SPI-21-001, and the accession number is FERM BP-22426 (accession date: 13 Aug. 2021).

Example 2

Cross-pollination was conducted using the Viroflay spinach variety, which lacks resistance to any race as the seed parent, and the SDF (RNR) line developed in Example 1 as the pollen parent. The thus obtained F1 individuals were subjected to inoculation tests using Pfs1, Pfs2, Pfs3, Pfs4, Pfs5, Pfs6, Pfs7, Pfs8, Pfs10, Pfs11, Pfs12, Pfs13, Pfs14, Pfs15, Pfs16, Pfs17, Pfs18, Pfs19 and the races indicated by the UA1014, Be2105B and PV2144 types, and the resistance to these races was investigated. Spinach is a dioecious species, but lines also exist which are monoecious, in which both pistillate and staminate flowers develop within the same individual. In the production of F1 seeds using Viroflay as the seed parent, seeds resulting from Viroflay self-pollination are sometimes also included in the harvest.

The genotype of the RPF-SK1 gene of each individual was determined by using genomic DNA extracted from each individual as a template, conducting PCR using the forward primer and reverse primer shown in Table 4 under conditions including one cycle at 94° C. for 60 seconds, followed by 35 cycles including 30 seconds at 94° C., 30 seconds at 62° C. and 60 seconds at 72° C., and then one cycle at 72° C. for 60 seconds, and then confirming the nucleotide sequence of the obtained PCR product using a sequencer.

TABLE 4

| Primer | Nucleotide sequence | SEQ ID NO |
|---|---|---|
| Forward primer | GGGTTATCTCAAATCACTGCCC | 1 |
| Reverse primer | TGAAGGTTGGCTGCGTTCA | 2 |

The results are shown in Table 5. In Table 5, "nt" means that no test was conducted, and no data is available. In the table cell for each race in the column for the "Viroflay" line, "–" indicates resistance and "+" indicates disease susceptibility. Of the RPF genotypes shown in Table 5, "RPF-SK1" means a resistant genotype derived from *Spinacia tetrandra*, and "rpf-0" means a susceptible genotype derived from Viroflay. Accordingly, "RPF-SK1/RPF-SK1" means a resistant homozygote, "rpf-O/rpf-0" means a susceptible homozygote, and "RPF-SK1/rpf-0" means a resistant and susceptible heterozygote.

TABLE 5

| | Line RPF genotype | SDF (RNR) RPF-SK1/RPF-SK1 | | Viroflay × SDF (RNR) F1 RPF-SK1/rpf-0 | | |
|---|---|---|---|---|---|---|
| | Number of individuals | Resistant individuals | Susceptible individuals | Resistant individuals | Susceptible individuals | Viroflay rpf-0/rpf-0 |
| Race - Pfs: | 1 | 40 | 0 | 30 | 7 | + |
| | 2 | 32 | 0 | 39 | 0 | + |
| | 3 | 28 | 0 | 29 | 0 | + |
| | 4 | 29 | 0 | 30 | 0 | + |
| | 5 | 18 | 0 | 20 | 0 | + |
| | 6 | 36 | 0 | 15 | 0 | + |
| | 7 | 28 | 0 | 29 | 0 | + |
| | 8 | 30 | 0 | 29 | 0 | + |
| | 9 | 29 | 0 | 30 | 0 | + |
| | 10 | 29 | 0 | 30 | 0 | + |
| | 11 | 29 | 0 | 30 | 0 | + |
| | 12 | 29 | 0 | 25 | 0 | + |
| | 13 | 30 | 0 | 28 | 0 | + |
| | 14 | 30 | 0 | 30 | 0 | + |
| | 15 | 36 | 0 | 28 | 0 | + |
| | 16 | 36 | 0 | 35 | 0 | + |
| | 17 | 40 | 0 | 20 | 0 | + |
| | 18 | 16 | 0 | 19 | 0 | + |
| | 19 | 34 | 0 | 42 | 0 | + |
| | UA1014 type | 24 | 0 | 27 | | + |
| | Be2105B type | 38 | 0 | 37 | 0 | + |
| | PV2144 type | 35 | 0 | 37 | 0 | + |

As illustrated in Table 5, the F1 individuals obtained by crossing Viroflay and the SDF (RNR) line exhibited resistance to all races. In the case of Pfs1, 7 individuals were identified as susceptible, but all of these individuals exhibited only slight disease on the cotyledons (a very low percentage within the rating from 5 to 50%), indicating a resistance reaction. Based on these results, it was clear that the RPF-SK1 gene was capable of imparting dominant resistance to at least Pfs1 to Pfs19 and the races indicated by the UA1014, Be2105B and PV2144 types.

Example 3

Cross-pollination was conducted using Viroflay as the seed parent, and the SDF (RNR) line developed in Example 1 as the pollen parent, and the thus obtained F1 seeds were self-pollinated to produce an F2 segregating population. This F2 population was subjected to inoculation tests using Pfs3, Pfs4, Pfs8, Pfs15 and the race indicated by UA1014 type, and the resistance to these races was investigated. The results are shown in Table 6. The genotypes and the like shown in the table have the same meaning as those in Table 5.

TABLE 6

| Line RPF genotype | | Viroflay × SDF (RNR) F2 Segregation RPF-SK1/RPF-SK1 RPF-SK1/rpf-0 rpf-0/rpf-0 | | | | |
|---|---|---|---|---|---|---|
| | Number of individuals | Resistant individuals | Susceptible individuals | Assumed mode of inheritance | $\chi^2$ test ($p > 0.05$) | Viroflay rpf-0/rpf-0 |
| Race - Pfs: | 3 | 31 | 13 | Single dominant gene | 0.486 | + |
| | 4 | 79 | 26 | Single dominant gene | 0.955 | + |
| | 8 | 37 | 8 | Single dominant gene | 0.263 | + |
| | 15 | 33 | 10 | Single dominant gene | 0.792 | + |
| | UA1014 type | 139 | 44 | Single dominant gene | 0.765 | + |

As illustrated in Table 6, the downy mildew resistance of the SDF (RNR) line to Pfs3, Pfs4, Pfs8, Pfs15 and UA1014 type segregated into a ratio of resistant individuals:susceptible individuals of close to 3:1. Accordingly, the RPF-SK1 gene was assumed to be a single dominant gene. This assumption was also supported by the results of the $\chi^2$ tests ($p>0.05$).

Example 4

Genetic analysis and gene marker development were carried out in order to specify the chromosome location region of the RPF-SK1 gene.

First, the Viroflay line and the SDF (RNR) line developed in Example 1 were crossed, and the thus obtained F1 were self-pollinated to produce an F2 segregating population.

From this F2 segregating population, 96 individuals were subjected to inoculation tests using the race indicated by UA1014 type to investigate resistance to this race. The results revealed 76 resistant individuals and 20 susceptible individuals.

Genetic analysis of these individuals was then conducted, and a search was conducted for the region within the genome responsible for resistant homozygosis or heterozygosis in the resistant individuals, or the region within the genome responsible for susceptible homozygosis in the susceptible individuals.

Individuals that had undergone investigation of their traits were used as a linkage analysis population, and genomic DNA was extracted from each individual. Genotyping was conducted using the DNA from the linkage analysis population and SNP markers designed for the SpinachBase reference genome. The genotyping was conducted using KASP genotyping assays.

Figure 1B:
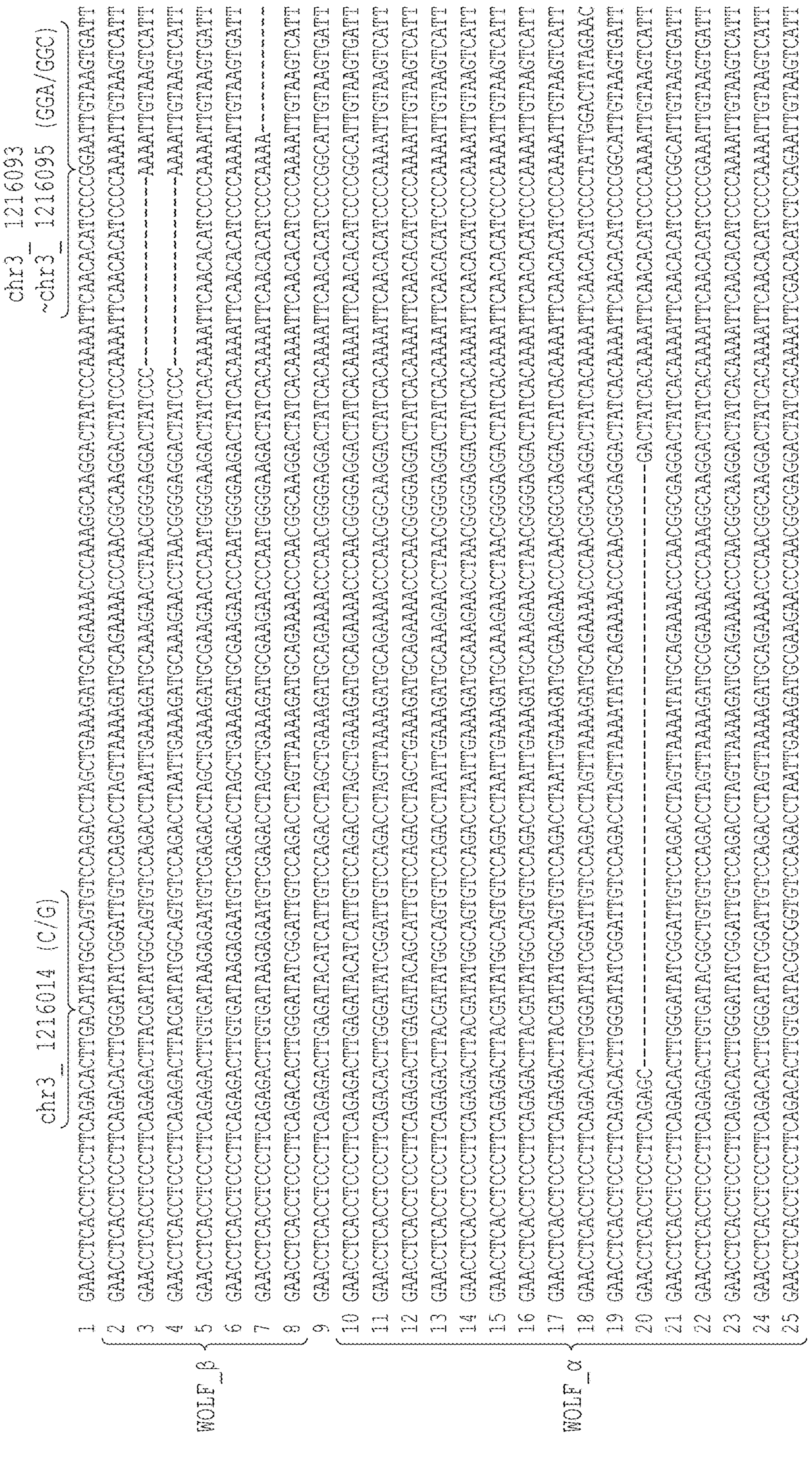
FIG. 1B is an alignment map in the vicinity of the RPF-SK1 gene locus of chromosome 3 (chr3_1215987 to chr3_1216108) of a spinach.
Figure 1C:
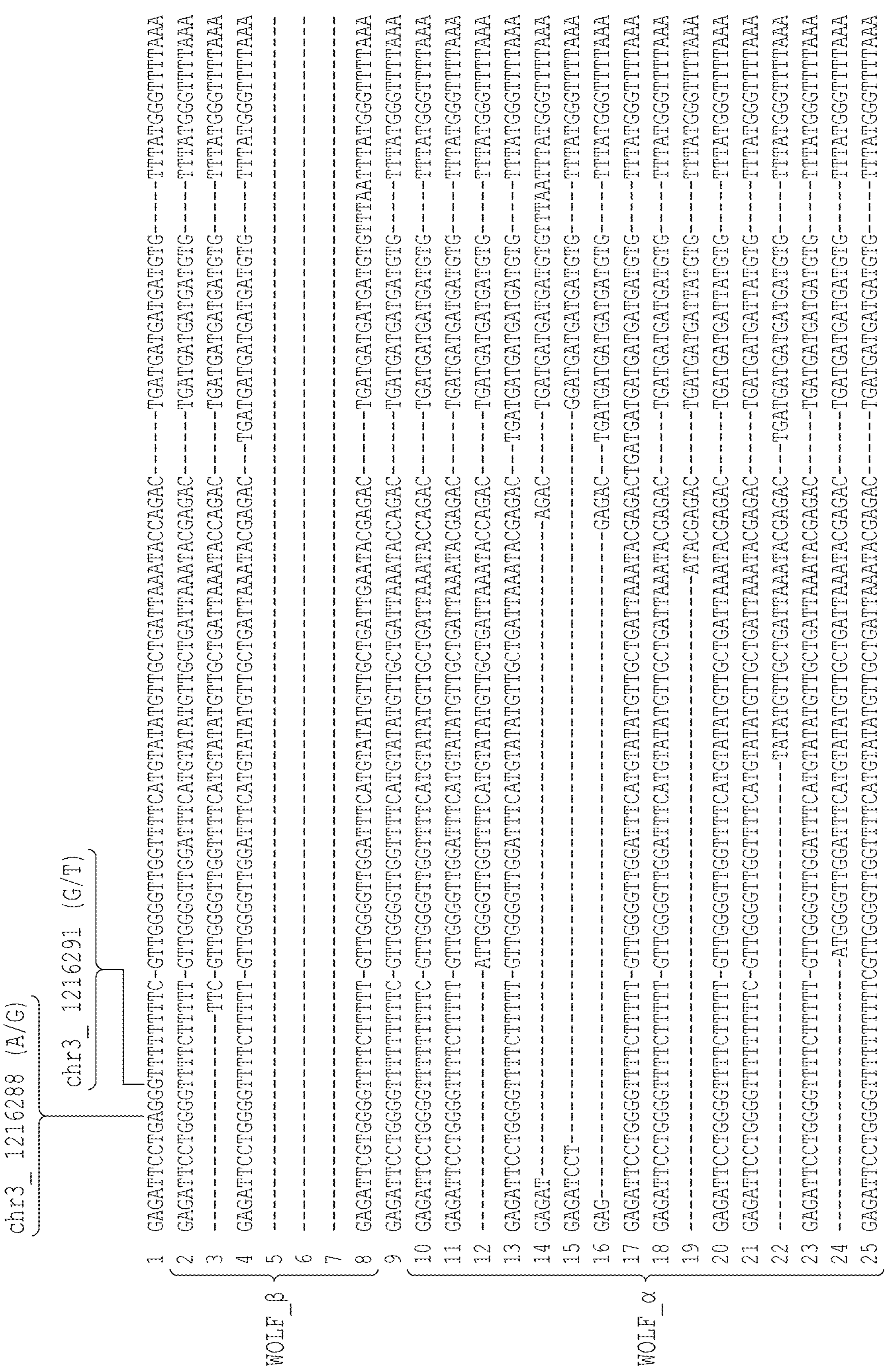
FIG. 1C is an alignment map in the vicinity of the RPF-SK1 gene locus of chromosome 3 (chr3_1216278 to chr3_1216376) of a spinach.
Figure 1E:
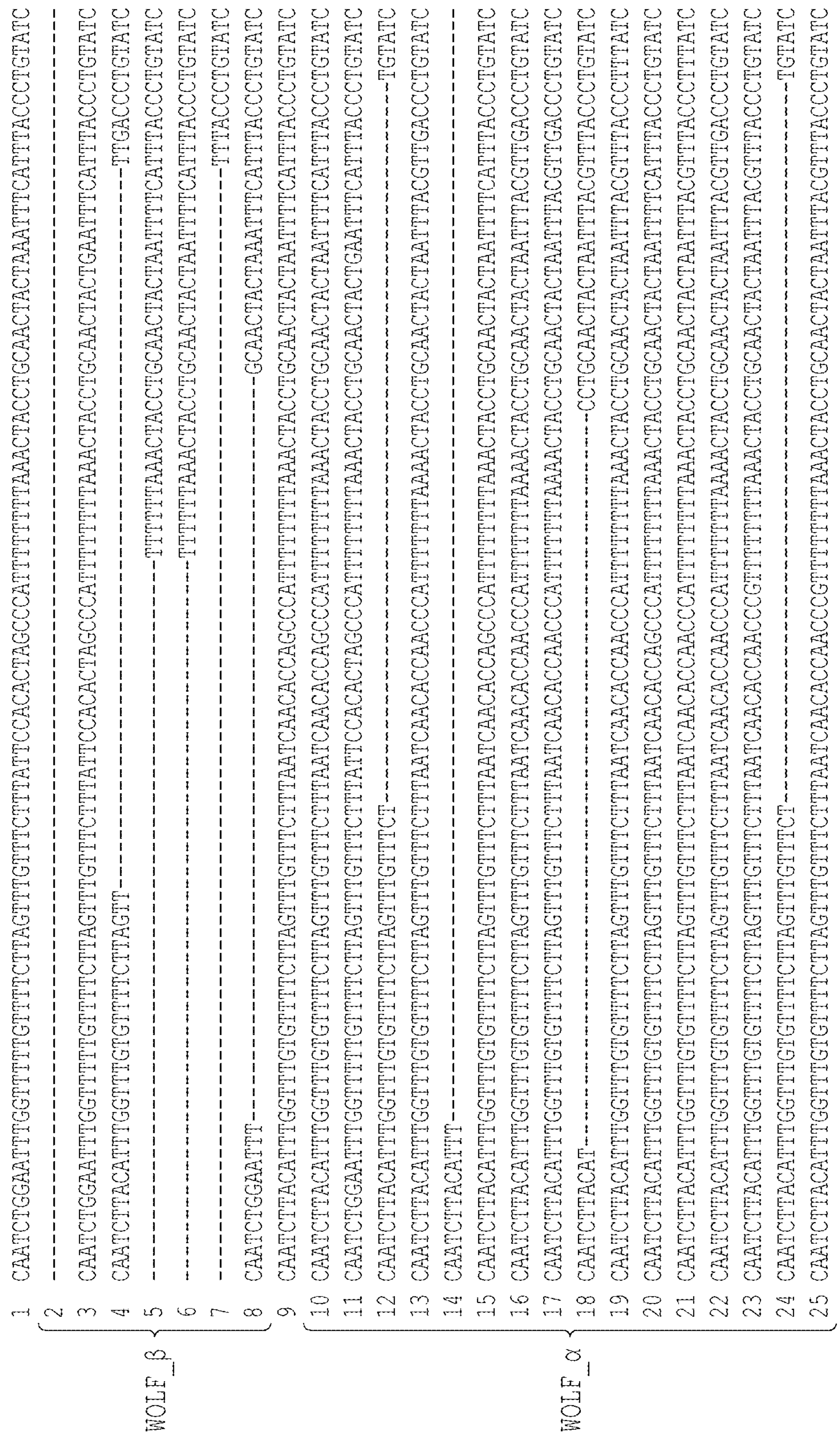
FIG. 1E is an alignment map in the vicinity of the RPF-SK1 gene locus of chromosome 3 (chr3_1216499 to chr3_1216602) of a spinach.

Sequence analysis of the RPF-SK1 gene confirmed that the region from chr3_1215795 to chr3_1216602 differed from the SpinachBase reference genome (Spinach genome sequence (v1)) and from the nucleotide sequences of the various WOLF genes disclosed in Patent Document 9. Alignment maps of the nucleotide sequences from chr3_1215795 to chr3_1216602 within chromosome 3 are illustrated in FIG. 1A to FIG. 1E. The numbers appended to each of the nucleotide sequences in FIG. 1 indicate the genes listed in Table 7.

TABLE 7

| Number in FIG. 1 | Gene name | SEQ ID NO |
|---|---|---|
| 1 | RPF-SK1 | 3-5 |
| 2 | CC-NBS-LRR_beta-WOLF0 genome | 6-8 |
| 3 | CC-NBS-LRR_beta-WOLF3 genome | 9-11 |
| 4 | CC-NBS-LRR_beta-WOLF5.1 genome | 12-14 |
| 5 | CC-NBS-LRR_beta-WOLF5.2 genome | 15-17 |
| 6 | CC-NBS-LRR_beta-WOLF6b genome | 18-20 |
| 7 | CC-NBS-LRR_beta-WOLF9 genome | 21-23 |
| 8 | CC-NBS-LRR_beta-WOLF11 genome | 24-26 |
| 9 | Spinach genome sequence (v1) | 27-29 |
| 10 | CC-NBS-LRR_alpha-WOLF7 genome | 30-32 |
| 11 | CC-NBS-LRR_alpha-WOLF2 genome | 33-35 |
| 12 | CC-NBS-LRR_alpha-WOLF2a genome | 36-38 |
| 13 | CC-NBS-LRR_alpha-WOLF6b genome | 39-41 |
| 14 | CC-NBS-LRR_alpha-WOLF4 genome | 42-44 |
| 15 | CC-NBS-LRR_alpha-WOLF4a genome | 45-47 |
| 16 | CC-NBS-LRR_alpha-WOLF6 genome. | 48-50 |
| 17 | CC-NBS-LRR_alpha-WOLF6c genome | 51-53 |
| 18 | CC-NBS-LRR_alpha-WOLF8 genome | 54-56 |
| 19 | CC-NBS-LRR_alpha-WOLF9 genome | 57-59 |
| 20 | CC-NBS-LRR_alpha-WOLF10 genome: | 60-62 |
| 21 | CC-NBS-LRR_alpha-WOLF11 genome | 63-65 |
| 22 | CC-NBS-LRR_alpha-WOLF12 genome | 66-68 |
| 23 | CC-NBS-LRR_alpha-WOLF15 genome | 69-71 |
| 24 | CC-NBS-LRR_alpha-WOLF16 genome | 72-74 |
| 25 | CC-NBS-LRR_alpha-WOLF18 genome | 75-77 |

These results revealed that in the homozygous RPF-SK1 gene of the SDF (RNR) line, the SNP identified by chr3_1215815 was cytosine, the SNP identified by chr3_1215855 was thymine, the SNP identified by chr3_1216014 was cytosine, the SNP identified by chr3_1216093 was guanine, the SNP identified by chr3_1216094 was guanine, the SNP identified by chr3_1216095 was adenine, the SNP identified by chr3_1216288 was adenine, and the SNP identified by chr3_1216291 was guanine. At these SNPs, the genotypes for the RPF-SK1 gene differed from the reference genome and from known WOLF (RPF) genes, confirming that the RPF-SK1 gene was a novel downy mildew resistance gene.

[Accession Numbers]

FERM BP-22426

[Sequence Listing]

PC35220_WA_sequences.xml

The invention claimed is:

1. A downy mildew resistant spinach plant having a downy mildew resistance RPF-SK1 gene in at least one allele, wherein in the RPF-SK1 gene:

(a) a SNP identified by chr3_1215815 is cytosine, (b) a SNP identified by chr3_1215855 is thymine, (c) a SNP identified by chr3_1216014 is cytosine, (d) a SNP identified by chr3_1216093 is guanine, a SNP identified by chr3_1216094 is guanine, and a SNP identified by chr3_1216095 is adenine, (e) a SNP identified by chr3_1216288 is adenine, and (f) a SNP identified by chr3_1216291 is guanine.

2. The downy mildew resistant spinach plant according to claim 1, wherein the RPF-SK1 gene is either homozygous or heterozygous.

3. The downy mildew resistant spinach plant according to claim 1, wherein the plant is resistant to at least downy mildew races Pfs1, Pfs2, Pfs3, Pfs4, Pfs5, Pfs6, Pfs7, Pfs8, Pfs9, Pfs10, Pfs11, Pfs12, Pfs13, Pfs14, Pfs15, Pfs16, Pfs17, Pfs18, Pfs19, and a race indicated by UA1014 type.

4. The downy mildew resistant spinach plant according to claim 1, wherein the plant is resistant to at least races indicated by downy mildew races indicated by Be2105B type and PV2144 type.

5. The downy mildew resistant spinach plant according to claim 1, wherein the downy mildew resistant spinach plant is derived from an interspecific hybrid plant of *Spinacia tetrandra* and a cultivated species of spinach.

6. The downy mildew resistant spinach plant according to claim 1, having downy mildew resistance derived from a plant specified in accession number FERM BP-22426.

7. The downy mildew resistant spinach plant according to claim 1, having at least one type of downy mildew resistance gene besides the RPF-SK1 gene.

8. A downy mildew resistant spinach plant that is a downy mildew resistant spinach plant specified in accession number FERM BP-22426, a hybrid plant obtained using the downy mildew resistant spinach plant as a parent, or a progeny of either of these plants.

9. A method for predicting downy mildew resistance of a spinach plant, or screening downy mildew resistant spinach plants, the method comprising investigating genotypes of at least one SNP selected from the group consisting of chr3_1215815, chr3_1215855, chr3_1216014, chr3_1216093, chr3_1216094, chr3_1216095, chr3_1216288 and chr3_1216291 of a test spinach plant, and predicting that the test spinach plant will have a high probability of exhibiting downy mildew resistance or selecting the test spinach plant as a downy mildew resistant spinach plant, in those cases where, in at least one allele:

(a) a SNP identified by chr3_1215815 is cytosine, (b) a SNP identified by chr3_1215855 is thymine, (c) a SNP identified by chr3_1216014 is cytosine, (d) a SNP identified by chr3_1216093 is guanine, a SNP identified by chr3_1216094 is guanine, and a SNP identified by chr3_1216095 is adenine, (e) a SNP identified by chr3_1216288 is adenine, and (f) a SNP identified by chr3_1216291 is guanine.

10. A method for producing the downy mildew resistant spinach plant according to claim 1, the method having:

a first crossing step of crossing a spinach plant having an RPF-SK1 gene and an arbitrary spinach plant, a second crossing step of obtaining a segregating population by subjecting an F1 individual obtained in the first crossing step to self-pollination, backcrossing, or interspecific crossing or intraspecific crossing with a spinach plant different from the parent used in the first crossing step, and a selection step of selecting a spinach plant having an RPF-SK1 gene from the segregating population.

11. A method for producing a downy mildew resistant spinach plant according to claim 10, wherein the arbitrary spinach plant, or the parent used in the interspecific crossing or intraspecific crossing in the second crossing step is a spinach plant having at least one type of downy mildew resistance gene besides the RPF-SK1 gene.

12. A portion of a plant body of the downy mildew resistant spinach plant according to claim 1.

13. A leaf the downy mildew resistant spinach plant according to claim 1.

14. A leaf the downy mildew resistant spinach plant according to claim 1.

15. A kit which is used for selecting the downy mildew resistant spinach plant according to claim 1, the kit comprising:

a forward primer and a reverse primer for conducting PCR amplification of a region including chr3_1215815 to chr3_1216291 of a test spinach plant, wherein the downy mildew resistant spinach plant has an RPF-SK1 gene.

* * * * *

SEQUENCE LISTING

```
Sequence total quantity: 77
SEQ ID NO: 1            moltype = DNA  length = 22
FEATURE                 Location/Qualifiers
source                  1..22
                        mol_type = other DNA
                        organism = synthetic construct
SEQUENCE: 1
gggttatctc aaatcactgc cc                                           22

SEQ ID NO: 2            moltype = DNA  length = 19
FEATURE                 Location/Qualifiers
source                  1..19
                        mol_type = other DNA
                        organism = synthetic construct
SEQUENCE: 2
tgaaggttgg ctgcgttca                                               19

SEQ ID NO: 3            moltype = DNA  length = 119
FEATURE                 Location/Qualifiers
source                  1..119
                        mol_type = genomic DNA
                        organism = Spinacia tetrandra
SEQUENCE: 3
gaaaattgaa tactcttata caatgacaag tctgcccatg gggatgcagt acttaacctc  60
tctccaaacc ctcgaactaa aatgttgtga tgaattgaat tcccttccag aatggataa   119

SEQ ID NO: 4            moltype = DNA  length = 122
FEATURE                 Location/Qualifiers
source                  1..122
                        mol_type = genomic DNA
                        organism = Spinacia tetrandra
SEQUENCE: 4
gaacctcacc tcccttcaga cacttgacat atggcagtgt ccagacctag ctgaaagatg  60
cagaaaaccc aaaggcaagg actatcccaa aattcaacac atccccggaa ttgtaagtga  120
tt                                                                 122

SEQ ID NO: 5            moltype = DNA  length = 325
FEATURE                 Location/Qualifiers
source                  1..325
                        mol_type = genomic DNA
                        organism = Spinacia tetrandra
SEQUENCE: 5
gagattcctg agggtttttt ttcgttgggg ttggttttca tgtatatgtt gctgattaaa  60
taccagactg atgatgatga tgtgtttatg ggttttaaat cagattaaat atatgggaaa  120
tgtaagttaa ttggggatgc acataaggtg tttgatgaaa tgtctattag aaatgttgtt  180
tcttggactt agaatgatat acactgtcgt cctttggttt ccaatctgga atttggtttt  240
tgttttctta gtttgtttct ttattccaca ctagcccatt ttttttaaac tacctgcaac  300
tactaaattt catttaccct gtatc                                        325

SEQ ID NO: 6            moltype = DNA  length = 119
FEATURE                 Location/Qualifiers
source                  1..119
                        mol_type = genomic DNA
                        organism = Spinacia sp.
SEQUENCE: 6
gagaattaaa gactctgaca aaatgacaag tttgcccatg gggatgcagt acttaacctc  60
cctccaaacc ctctatctac accattgtta tgaattgaat tcccttccag aatggataa   119

SEQ ID NO: 7            moltype = DNA  length = 122
FEATURE                 Location/Qualifiers
source                  1..122
                        mol_type = genomic DNA
                        organism = Spinacia sp.
SEQUENCE: 7
gaacctcacc tcccttcaga cacttgggat atcggattgt ccagacctag ttaaaagatg  60
cagaaaaccc aacggcaagg actatcccaa aattcaacac atccccaaaa ttgtaagtca  120
tt                                                                 122

SEQ ID NO: 8            moltype = DNA  length = 214
FEATURE                 Location/Qualifiers
source                  1..214
                        mol_type = genomic DNA
```

```
                         organism = Spinacia sp.
SEQUENCE: 8
gagattcctg gggttttctt tttgttgggg ttggatttca tgtatatgtt gctgattaaa  60
tacgagactg atgatgatga tgtgtttatg ggttttaaat cagattaaat atatgggaaa  120
tgtaagttag ttggggatgc acataaggtg tttgatgaaa tgtctatgag aaatgttgtt  180
tcttggactt agaatgatat acactgtcgt cctt                              214

SEQ ID NO: 9             moltype = DNA  length = 119
FEATURE                  Location/Qualifiers
source                   1..119
                         mol_type = genomic DNA
                         organism = Spinacia sp.
SEQUENCE: 9
ggaaattaat tactctgaca aaatgacaag ttttcccatg gggatgcagt acttaacctc  60
cctccaaacc atccatcttt atgattgtta taaattgaat tccattccag aatggataa   119

SEQ ID NO: 10            moltype = DNA  length = 104
FEATURE                  Location/Qualifiers
source                   1..104
                         mol_type = genomic DNA
                         organism = Spinacia sp.
SEQUENCE: 10
gaacctcacc tcccttcaga gacttacgat atggcagtgt ccagacctaa ttgaaagatg  60
caaagaacct aacggggagg actatcccaa aattgtaagt catt                   104

SEQ ID NO: 11            moltype = DNA  length = 305
FEATURE                  Location/Qualifiers
source                   1..305
                         mol_type = genomic DNA
                         organism = Spinacia sp.
SEQUENCE: 11
ttcgttgggg ttggttttca tgtatatgtt gctgattaaa taccagactg atgatgatga  60
tgtgtttatg ggttttaaat cagattaaat atatgggaaa tgtaagttaa ttggggatgc  120
acataaggtg tttgatgaaa tgtctattag aaatgttgtt tcttggactt agaatgatat  180
acactgtcgt cctttggttt ccaatctgga atttggtttt tgttttctta gtttgtttct  240
ttattccaca ctagcccatt ttttttaaac tacctgcaac tactgaattt catttaccct  300
gtatc                                                              305

SEQ ID NO: 12            moltype = DNA  length = 119
FEATURE                  Location/Qualifiers
source                   1..119
                         mol_type = genomic DNA
                         organism = Spinacia sp.
SEQUENCE: 12
ggaaattaat tactctgaca aaatgacaag ttttcccatg gggatgcagt acttaacctc  60
cctccaaacc atccatcttt atgattgtta taaattgaat tccattccag aatggataa   119

SEQ ID NO: 13            moltype = DNA  length = 104
FEATURE                  Location/Qualifiers
source                   1..104
                         mol_type = genomic DNA
                         organism = Spinacia sp.
SEQUENCE: 13
gaacctcacc tcccttcaga gacttacgat atggcagtgt ccagacctaa ttgaaagatg  60
caaagaacct aacggggagg actatcccaa aattgtaagt catt                   104

SEQ ID NO: 14            moltype = DNA  length = 256
FEATURE                  Location/Qualifiers
source                   1..256
                         mol_type = genomic DNA
                         organism = Spinacia sp.
SEQUENCE: 14
gagattcctg gggttttctt tttgttgggg ttggatttca tgtatatgtt gctgattaaa  60
tacgagactg atgatgatga tgatgtgttt atgggtttta aatcagatta aatatatggg  120
aaatgtaagt taatttggga tgcacataag gtgtttgctg aaatgtctat gagaaatgtt  180
gtttcttgga cttagaatga tatacactgt cgtccattgg tttccaatct tacatttggt  240
ttgtgttttc ttagtt                                                  256

SEQ ID NO: 15            moltype = DNA  length = 119
FEATURE                  Location/Qualifiers
source                   1..119
                         mol_type = genomic DNA
                         organism = Spinacia sp.
SEQUENCE: 15
gaaaattgaa tactcttata aaatgacaag tctgcccatg gggatgcagt acttaacctc  60
cctccaaacc ctcgaactaa aatgttgtga tgaattgaat tcccttccag aatggataa   119

SEQ ID NO: 16            moltype = DNA  length = 122
FEATURE                  Location/Qualifiers
```

```
source                  1..122
                        mol_type = genomic DNA
                        organism = Spinacia sp.
SEQUENCE: 16
gaacctcacc tcccttcaga gacttgtgat aagagaatgt cgagacctag ctgaaagatg  60
cgaagaaccc aatggggaag actatcacaa aattcaacac atccccaaaa ttgtaagtga  120
tt                                                                 122

SEQ ID NO: 17           moltype = DNA  length = 45
FEATURE                 Location/Qualifiers
source                  1..45
                        mol_type = genomic DNA
                        organism = Spinacia sp.
SEQUENCE: 17
ttttttaaac tacctgcaac tactaatttt catttaccct gtatc                  45

SEQ ID NO: 18           moltype = DNA  length = 119
FEATURE                 Location/Qualifiers
source                  1..119
                        mol_type = genomic DNA
                        organism = Spinacia sp.
SEQUENCE: 18
gaaaattgaa tactcttata aaatgacaag tctgcccatg gggatgcagt acttaacctc  60
cctccaaacc ctcgaactaa aatgttgtga tgaattgaat tcccttccag aatggataa   119

SEQ ID NO: 19           moltype = DNA  length = 122
FEATURE                 Location/Qualifiers
source                  1..122
                        mol_type = genomic DNA
                        organism = Spinacia sp.
SEQUENCE: 19
gaacctcacc tcccttcaga gacttgtgat aagagaatgt cgagacctag ctgaaagatg  60
cgaagaaccc aatggggaag actatcacaa aattcaacac atccccaaaa ttgtaagtga  120
tt                                                                 122

SEQ ID NO: 20           moltype = DNA  length = 45
FEATURE                 Location/Qualifiers
source                  1..45
                        mol_type = genomic DNA
                        organism = Spinacia sp.
SEQUENCE: 20
ttttttaaac tacctgcaac tactaatttt catttaccct gtatc                  45

SEQ ID NO: 21           moltype = DNA  length = 119
FEATURE                 Location/Qualifiers
source                  1..119
                        mol_type = genomic DNA
                        organism = Spinacia sp.
SEQUENCE: 21
gaaaattgaa tactcttata aaatgacaag tctgcccatg gggatgcagt acttaacctc  60
cctccaaacc ctcgaactaa aatgttgtga tgaattgaat tcccttccag aatggataa   119

SEQ ID NO: 22           moltype = DNA  length = 110
FEATURE                 Location/Qualifiers
source                  1..110
                        mol_type = genomic DNA
                        organism = Spinacia sp.
SEQUENCE: 22
gaacctcacc tcccttcaga gacttgtgat aagagaatgt cgagacctag ctgaaagatg  60
cgaagaaccc aatggggaag actatcacaa aattcaacac atccccaaaa             110

SEQ ID NO: 23           moltype = DNA  length = 22
FEATURE                 Location/Qualifiers
source                  1..22
                        mol_type = genomic DNA
                        organism = Spinacia sp.
SEQUENCE: 23
tttcttagat ttaccctgta tc                                           22

SEQ ID NO: 24           moltype = DNA  length = 119
FEATURE                 Location/Qualifiers
source                  1..119
                        mol_type = genomic DNA
                        organism = Spinacia sp.
SEQUENCE: 24
gagaattaaa gactctgaca aaatgacaag tttgcccatg gggatgcagt acttaacctc  60
cctccaaacc ctctatctac accattgtta tgaattgaat tcccttccag aatggataa   119

SEQ ID NO: 25           moltype = DNA  length = 122
```

```
FEATURE                Location/Qualifiers
source                 1..122
                       mol_type = genomic DNA
                       organism = Spinacia sp.
SEQUENCE: 25
gaacctcacc tcccttcaga cacttgggat atcggattgt ccagacctag ttaaaagatg  60
cagaaaaccc aacggcaagg actatcccaa aattcaacac atccccaaaa ttgtaagtca  120
tt                                                                 122

SEQ ID NO: 26          moltype = DNA  length = 269
FEATURE                Location/Qualifiers
source                 1..269
                       mol_type = genomic DNA
                       organism = Spinacia sp.
SEQUENCE: 26
gagattcgtg gggttttctt tttgttgggg ttggatttca tgtatatgtt gctgattgaa  60
tacgagactg atgatgatga tgtgtttaat ttatgggttt taaatcagat taaatatatg  120
ggaaatgtaa gttaattggg gatgcacata aggtgtttga tgaaatgtct attagaaatg  180
ttgtttcttg gacttagaat gatatacact gtcgtccttt ggtttccaat ctggaatttg  240
caactactaa atttcattta ccctgtatc                                    269

SEQ ID NO: 27          moltype = DNA  length = 119
FEATURE                Location/Qualifiers
source                 1..119
                       mol_type = genomic DNA
                       organism = Spinacia sp.
SEQUENCE: 27
gagaattgaa gactctgaca aaatgacaag tttgcccatg gggatgcagt acttaacctc  60
cctccaaacc ctctatctat catattgtga tgaattgaat tcccttccag aatggataa   119

SEQ ID NO: 28          moltype = DNA  length = 122
FEATURE                Location/Qualifiers
source                 1..122
                       mol_type = genomic DNA
                       organism = Spinacia sp.
SEQUENCE: 28
gaacctcacc tcccttcaga gacttgagat acatcattgt ccagacctag ctgaaagatg  60
cagaaaaccc aacggggagg actatcccaa aattcaacac atccccggca ttgtaagtga  120
tt                                                                 122

SEQ ID NO: 29          moltype = DNA  length = 325
FEATURE                Location/Qualifiers
source                 1..325
                       mol_type = genomic DNA
                       organism = Spinacia sp.
SEQUENCE: 29
gagattcctg gggttttttt ttcgttgggg ttggttttca tgtatatgtt gctgattaaa  60
taccagactg atgatgatga tgtgtttatg ggttttaaat cagattaaat atatgggaaa  120
tgtaagttag ttggggatgc acataaggtg tttgatgaaa tgtctattag aaatgttgtt  180
tcttggactt agaatgatat acactgtcgt cctttggttt ccaatcttac atttggtttg  240
tgttttctta gtttgtttct ttaatcaaca ccagcccatt ttttttaaac tacctgcaac  300
tactaatttt catttaccct gtatc                                        325

SEQ ID NO: 30          moltype = DNA  length = 119
FEATURE                Location/Qualifiers
source                 1..119
                       mol_type = genomic DNA
                       organism = Spinacia sp.
SEQUENCE: 30
gagaattgaa gactctgaca aaatgacaag tttgcccatg gggatgcagt acttaacctc  60
cctccaaacc ctctatctat catattgtga tgaattgaat tcccttccag aatggataa   119

SEQ ID NO: 31          moltype = DNA  length = 122
FEATURE                Location/Qualifiers
source                 1..122
                       mol_type = genomic DNA
                       organism = Spinacia sp.
SEQUENCE: 31
gaacctcacc tcccttcaga gacttgagat acatcattgt ccagacctag ctgaaagatg  60
cagaaaaccc aacggggagg actatcccaa aattcaacac atccccggca ttgtaagtga  120
tt                                                                 122

SEQ ID NO: 32          moltype = DNA  length = 325
FEATURE                Location/Qualifiers
source                 1..325
                       mol_type = genomic DNA
                       organism = Spinachia sp.
SEQUENCE: 32
gagattcctg gggttttttt ttcgttgggg ttggttttca tgtatatgtt gctgattaaa  60
```

```
taccagactg atgatgatga tgtgtttatg ggttttaaat cagattaaat atatgggaaa  120
tgtaagttag ttggggatgc acataaggtg tttgatgaaa tgtctattag aaatgttgtt  180
tcttggactt agaatgatat acactgtcgt cctttggttt ccaatcttac atttggtttg  240
tgttttctta gtttgtttct ttaatcaaca ccagcccatt ttttttaaac tacctgcaac  300
tactaatttt catttaccct gtatc                                         325

SEQ ID NO: 33          moltype = DNA  length = 119
FEATURE                Location/Qualifiers
source                 1..119
                       mol_type = genomic DNA
                       organism = Spinacia sp.
SEQUENCE: 33
ggaaattgaa aactcttaca aaatgacaag tttgcccatg gggatgcagt acttaacctc  60
cctccaaacc ctctatctac accattgtta tgaattgaat tcccttccag aatggataa   119

SEQ ID NO: 34          moltype = DNA  length = 122
FEATURE                Location/Qualifiers
source                 1..122
                       mol_type = genomic DNA
                       organism = Spinacia sp.
SEQUENCE: 34
gaacctcacc tcccttcaga cacttgggat atcggattgt ccagacctag ttaaaagatg  60
cagaaaaccc aacggcaagg actatcccaa aattcaacac atccccaaaa ttgtaagtca  120
tt                                                                  122

SEQ ID NO: 35          moltype = DNA  length = 266
FEATURE                Location/Qualifiers
source                 1..266
                       mol_type = genomic DNA
                       organism = Spinacia sp.
SEQUENCE: 35
gagattcctg gggttttctt tttgttgggg ttggatttca tgtatatgtt gctgattaaa  60
tacgagactg atgatgatga tgtgtttatg ggttttaaat cagattaaat atatgggaaa  120
tgtaagttag ttggggatgc acataaggtg tttgatggtt tccaatctgg aatttggttt  180
ttgttttctt agtttgtttc tttattccac actagcccat ttttttttaaa ctacctgcaa  240
ctactgaatt tcatttaccc tgtatc                                        266

SEQ ID NO: 36          moltype = DNA  length = 119
FEATURE                Location/Qualifiers
source                 1..119
                       mol_type = genomic DNA
                       organism = Spinacia sp.
SEQUENCE: 36
ggaaattaaa ggctcttgca aaatgacaag tttgcccatg gggatgcagt acttaacctc  60
cctccaaacc ctccatctat catattgtga tgaattgaat tcccttccag aatggataa   119

SEQ ID NO: 37          moltype = DNA  length = 122
FEATURE                Location/Qualifiers
source                 1..122
                       mol_type = genomic DNA
                       organism = Spinacia sp.
SEQUENCE: 37
gaacctcacc tcccttcaga gacttgagat acagcattgt ccagacctag ctgaaagatg  60
cagaaaaccc aacggggagg actatcccaa aattcaacac atccccaaaa ttgtaagtca  120
tt                                                                  122

SEQ ID NO: 38          moltype = DNA  length = 243
FEATURE                Location/Qualifiers
source                 1..243
                       mol_type = genomic DNA
                       organism = Spinacia sp.
SEQUENCE: 38
attggggttg gttttcatgt atatgttgct gattaaatac cagactgatg atgatgatgt  60
gtttatgggt tttaaatcag attaaatata tgggaaatgt aagttaattg gggatgcaca  120
taaggtgttt gatgaaatgt ctatgagaaa tgttgtttct tggacttaga atgatataca  180
ctgtcgtcct ttggtttcca atcttacatt tggtttgtgt tttcttagtt tgtttcttgt  240
atc                                                                 243

SEQ ID NO: 39          moltype = DNA  length = 119
FEATURE                Location/Qualifiers
source                 1..119
                       mol_type = genomic DNA
                       organism = Spinacia sp.
SEQUENCE: 39
gagaattaaa gactctgaca aaatgacaag tttgcccatg gggatgcagt acttaacctc  60
cctccaaacc ctctatctac accattgtta tgaattgaat tcccttccag aatggataa   119

SEQ ID NO: 40          moltype = DNA  length = 122
FEATURE                Location/Qualifiers
```

```
source                 1..122
                       mol_type = genomic DNA
                       organism = Spinacia sp.
SEQUENCE: 40
gaacctcacc tcccttcaga gacttacgat atggcagtgt ccagacctaa ttgaaagatg  60
caaagaacct aacggggagg actatcccaa aattcaacac atccccaaaa ttgtaagtca  120
tt                                                                 122

SEQ ID NO: 41          moltype = DNA  length = 328
FEATURE                Location/Qualifiers
source                 1..328
                       mol_type = genomic DNA
                       organism = Spinacia sp.
SEQUENCE: 41
gagattcctg ggttttcttt tttgttgggg ttggatttca tgtatatgtt gctgattaaa  60
tacgagactg atgatgatga tgatgtgttt atgggtttta aatcagatta aatatatggg  120
aaatgtaagt taatttggga tgcacataag gtgtttgctg aaatgtctat gagaaatgtt  180
gtttcttgga cttagaatga tatacactgt cgtccattgg tttccaatct tacatttggt  240
ttgtgttttc ttagtttgtt tctttaatca acaccaaccc attttttttaa aactacctgc  300
aactactaat ttacgttgac cctgtatc                                     328

SEQ ID NO: 42          moltype = DNA  length = 119
FEATURE                Location/Qualifiers
source                 1..119
                       mol_type = genomic DNA
                       organism = Spinacia sp.
SEQUENCE: 42
gagaattgaa gactctgaca aaatgacaag ttttcccatg ggatgcagt acttaacctc  60
cctccaaacc atccatcttt atgattgtta taaattgaat tccattccag aatggataa   119

SEQ ID NO: 43          moltype = DNA  length = 122
FEATURE                Location/Qualifiers
source                 1..122
                       mol_type = genomic DNA
                       organism = Spinacia sp.
SEQUENCE: 43
gaacctcacc tcccttcaga gacttacgat atggcagtgt ccagacctaa ttgaaagatg  60
caaagaacct aacggggagg actatcccaa aattcaacac atccccaaaa ttgtaagtca  120
tt                                                                 122

SEQ ID NO: 44          moltype = DNA  length = 180
FEATURE                Location/Qualifiers
source                 1..180
                       mol_type = genomic DNA
                       organism = Spinacia sp.
SEQUENCE: 44
gagatagact gatgatgatg atgtgtttaa tttatgggtt ttaaatcaga ttaaatatat  60
gggaaatgta agttaattgg ggatgcacat aaggtgtttg atgaaatgtc tattagaaat  120
gttgtttctt ggacttagaa tgatatacac tgtcgtcctt tggtttccaa tcttacattt  180

SEQ ID NO: 45          moltype = DNA  length = 119
FEATURE                Location/Qualifiers
source                 1..119
                       mol_type = genomic DNA
                       organism = Spinacia sp.
SEQUENCE: 45
gagaattgaa gactctgaca aaatgacaag tttgcccatg ggatgcagt acttaacctc  60
cctccaaacc ctctatctac accattgtta tgaattgaat tcccttccag aatggataa   119

SEQ ID NO: 46          moltype = DNA  length = 122
FEATURE                Location/Qualifiers
source                 1..122
                       mol_type = genomic DNA
                       organism = Spinacia sp.
SEQUENCE: 46
gaacctcacc tcccttcaga gacttacgat atggcagtgt ccagacctaa ttgaaagatg  60
caaagaacct aacggggagg actatcccaa aattcaacac atccccaaaa ttgtaagtca  120
tt                                                                 122

SEQ ID NO: 47          moltype = DNA  length = 265
FEATURE                Location/Qualifiers
source                 1..265
                       mol_type = genomic DNA
                       organism = Spinacia sp.
SEQUENCE: 47
gagatcctgg atgatgatga tgtgtttatg ggttttaaat cagattaaat atatgggaaa  60
tgtaagttaa ttggggatgc acataaggtg tttgatgaaa tgtctatgag aaatgttgtt  120
tcttggactt agaatgatat acactgtcgt cctttggttt ccaatcttac atttggtttg  180
tgttttctta gtttgtttct ttaatcaaca ccagcccatt ttttttaaac tacctgcaac  240
```

```
tactaatttt catttaccct gtatc                                  265

SEQ ID NO: 48          moltype = DNA  length = 119
FEATURE                Location/Qualifiers
source                 1..119
                       mol_type = genomic DNA
                       organism = Spinacia sp.
SEQUENCE: 48
gagaattaaa gactctgaca aaatgacaag tttgcccatg gggatgcagt acttaacctc  60
cctccaaacc ctctatctac accattgtta tgaattgaat tcccttccag aatggataa   119

SEQ ID NO: 49          moltype = DNA  length = 122
FEATURE                Location/Qualifiers
source                 1..122
                       mol_type = genomic DNA
                       organism = Spinacia sp.
SEQUENCE: 49
gaacctcacc tcccttcaga gacttacgat atggcagtgt ccagacctaa ttgaaagatg  60
caaagaacct aacggggagg actatcccaa aattcaacac atccccaaaa ttgtaagtca  120
tt                                                                 122

SEQ ID NO: 50          moltype = DNA  length = 268
FEATURE                Location/Qualifiers
source                 1..268
                       mol_type = genomic DNA
                       organism = Spinacia sp.
SEQUENCE: 50
gaggagactg atgatgatga tgatgtgttt atgggtttta aatcagatta aatatatggg  60
aaatgtaagt taatttggga tgcacataag gtgtttgctg aaatgtctat gagaaatgtt  120
gtttcttgga cttagaatga tatacactgt cgtccattgg tttccaatct tacatttggt  180
ttgtgttttc ttagtttgtt tctttaatca acaccaaccc attttttaa aactacctgc   240
aactactaat ttacgttgac cctgtatc                                     268

SEQ ID NO: 51          moltype = DNA  length = 119
FEATURE                Location/Qualifiers
source                 1..119
                       mol_type = genomic DNA
                       organism = Spinacia sp.
SEQUENCE: 51
gagaattaaa gactctgaca aaatgacaag tttgcccatg gggatgcagt acttaacctc  60
cctccaaacc ctctatctac accattgtta tgaattgaat tcccttccag aatggataa   119

SEQ ID NO: 52          moltype = DNA  length = 122
FEATURE                Location/Qualifiers
source                 1..122
                       mol_type = genomic DNA
                       organism = Spinacia sp.
SEQUENCE: 52
gaacctcacc tcccttcaga gacttacgat atggcagtgt ccagacctaa ttgaaagatg  60
cgaagaaccc aacggcgagg actatcccaa aattcaacac atccccaaaa ttgtaagtca  120
tt                                                                 122

SEQ ID NO: 53          moltype = DNA  length = 331
FEATURE                Location/Qualifiers
source                 1..331
                       mol_type = genomic DNA
                       organism = Spinacia sp.
SEQUENCE: 53
gagattcctg gggttttctt tttgttgggg ttggatttca tgtatatgtt gctgattaaa  60
tacgagactg atgatgatga tgatgatgtg tttatgggtt ttaaatcaga ttaaatatat  120
gggaaatgta agttaatttg ggatgcacat aaggtgtttg ctgaaatgtc tatgagaaat  180
gttgtttctt ggacttagaa tgatatacac tgtcgtccat tggtttccaa tcttacattt  240
ggtttgtgtt ttcttagttt gtttctttaa tcaacaccaa cccatttttt taaaactacc  300
tgcaactact aatttacgtt gaccctgtat c                                 331

SEQ ID NO: 54          moltype = DNA  length = 119
FEATURE                Location/Qualifiers
source                 1..119
                       mol_type = genomic DNA
                       organism = Spinacia sp.
SEQUENCE: 54
gagaattaaa gactctgaca aaatgacaag tttgcccatg gggatgcagt acttaacctc  60
cctccaaacc ctctatctac accattgtta tgaattgaat tcccttccag aatggataa   119

SEQ ID NO: 55          moltype = DNA  length = 122
FEATURE                Location/Qualifiers
source                 1..122
                       mol_type = genomic DNA
                       organism = Spinacia sp.
```

```
SEQUENCE: 55
gaacctcacc tcccttcaga cacttgggat atcggattgt ccagacctag ttaaaagatg  60
cagaaaaccc aacggcaagg actatcccaa aattcaacac atcccctatt ggagtataga  120
ac                                                                 122

SEQ ID NO: 56          moltype = DNA  length = 265
FEATURE                Location/Qualifiers
source                 1..265
                       mol_type = genomic DNA
                       organism = Spinacia sp.
SEQUENCE: 56
gagattcctg gggttttctt tttgttgggg ttggatttca tgtatatgtt gctgattaaa  60
tacgagactg atgatgatga tgtgtttatg ggttttaaat cagattaaat atatgggaaa  120
tgcaagttaa tttgggatgc acataaggtg tttgctgaaa tgtctatgag aaatgttgtt  180
tcttggactt agaatgatat acactgtcgt cctttggttt ccaatcttac atcctgcaac  240
tactaattta cgtttaccct gtatc                                        265

SEQ ID NO: 57          moltype = DNA  length = 119
FEATURE                Location/Qualifiers
source                 1..119
                       mol_type = genomic DNA
                       organism = Spinacia sp.
SEQUENCE: 57
gagaattaaa gactctgaca aaatgacaag tttgcccatg ggatgcagt acttaacctc  60
cctccaaacc ctcgaactat catattgtga tgaattgaat tcccttccag aatggataa   119

SEQ ID NO: 58          moltype = DNA  length = 122
FEATURE                Location/Qualifiers
source                 1..122
                       mol_type = genomic DNA
                       organism = Spinacia sp.
SEQUENCE: 58
gaacctcacc tcccttcaga cacttgggat atcggattgt ccagacctag ttaaaatatg  60
cagaaaaccc aacggcgagg actatcccaa aattcaacac atccccggca ttgtaagtga  120
tt                                                                 122

SEQ ID NO: 59          moltype = DNA  length = 266
FEATURE                Location/Qualifiers
source                 1..266
                       mol_type = genomic DNA
                       organism = Spinacia sp.
SEQUENCE: 59
atacgagact gatgatgatt atgtgtttat gggttttaaa tcagattaaa tatatggaaa  60
atgtaagtta gttggggatg cacataaggt gtttgatgaa atgtctttta gaaatgttgt  120
ttcttggact tagaatgata tacactgtcg tcctttggtt tccaatctta catttggttt  180
gtgttttctt agtttgtttc tttaatcaac accaacccat ttttttaaa ctacctgcaa  240
ctactaattt acgtttaccc tttatc                                       266

SEQ ID NO: 60          moltype = DNA  length = 119
FEATURE                Location/Qualifiers
source                 1..119
                       mol_type = genomic DNA
                       organism = Spinacia sp.
SEQUENCE: 60
ggaaattaaa tactctgaca aaatgacaag tttgcccatg ggatgcagt acttaacctc  60
cctccaaacc atccatcttt attgttgtgg taaattgaat tccattccag aatggataa   119

SEQ ID NO: 61          moltype = DNA  length = 65
FEATURE                Location/Qualifiers
source                 1..65
                       mol_type = genomic DNA
                       organism = Spinacia sp.
SEQUENCE: 61
gaacctcacc tcccttcaga gcgactatcc caaaattcaa cacatcccca aaattgtaag  60
tcatt                                                              65

SEQ ID NO: 62          moltype = DNA  length = 325
FEATURE                Location/Qualifiers
source                 1..325
                       mol_type = genomic DNA
                       organism = Spinacia sp.
SEQUENCE: 62
gagattcctg gggttttctt tttgttgggg ttggttttca tgtatatgtt gctgattaaa  60
tacgagactg atgatgatta tgtgtttatg ggttttaaat cagattaaat atatggaaaa  120
tgtaagttag ttggggatgc acataaggtg tttgatgaaa tgtctattag aaatgttgtt  180
tcttggactt agaatgatat acactgtcgt cctttggttt ccaatcttac atttggtttg  240
tgttttctta gtttgtttct ttaatcaaca ccagcccatt ttttttaaac tacctgcaac  300
tactaatttt catttaccct gtatc                                        325
```

```
SEQ ID NO: 63          moltype = DNA  length = 119
FEATURE                Location/Qualifiers
source                 1..119
                       mol_type = genomic DNA
                       organism = Spinacia sp.
SEQUENCE: 63
ggaaattaaa ggctcttgca aaatgacaag tttgcccatg gggatgcagt acttaacctc  60
cctccaaacc ctcgaactat catattgtga tgaattgaat tcccttccag aatggataa   119

SEQ ID NO: 64          moltype = DNA  length = 122
FEATURE                Location/Qualifiers
source                 1..122
                       mol_type = genomic DNA
                       organism = Spinacia sp.
SEQUENCE: 64
gaacctcacc tcccttcaga cacttgggat atcggattgt ccagacctag ttaaaatatg  60
cagaaaaccc aacggcgagg actatcccaa aattcaacac atccccggca ttgtaagtga  120
tt                                                                 122

SEQ ID NO: 65          moltype = DNA  length = 325
FEATURE                Location/Qualifiers
source                 1..325
                       mol_type = genomic DNA
                       organism = Spinacia sp.
SEQUENCE: 65
gagattcctg gggttttttt ttcgttgggg ttggttttca tgtatatgtt gctgattaaa  60
tacgagactg atgatgatta tgtgtttatg ggttttaaat cagattaaat atatggaaaa  120
tgtaagttag ttggggatgc acataaggtg tttgatgaaa tgtctattag aaatgttgtt  180
tcttggactt agaatgatat acactgtcgt cctttggttt ccaatcttac atttggtttg  240
tgttttctta gtttgtttct ttaatcaaca ccaacccatt ttttttaaac tacctgcaac  300
tactaattta cgtttaccct ttatc                                        325

SEQ ID NO: 66          moltype = DNA  length = 119
FEATURE                Location/Qualifiers
source                 1..119
                       mol_type = genomic DNA
                       organism = Spinacia sp.
SEQUENCE: 66
ggaaattaaa ggctcttgca aaatgacaag tttgcccatg gggatgcagt acttaacctc  60
cctccaaacc ctcaaactag aaaattgtga tgaattgaat tcccttccag aatggataa   119

SEQ ID NO: 67          moltype = DNA  length = 122
FEATURE                Location/Qualifiers
source                 1..122
                       mol_type = genomic DNA
                       organism = Spinacia sp.
SEQUENCE: 67
gaacctcacc tcccttcaga gacttgtgat acggctgtgt ccagacctag ttaaaagatg  60
cggaaaaccc aaaggcaagg actatcccaa aattcaacac atccccgaaa ttgtaagtga  120
tt                                                                 122

SEQ ID NO: 68          moltype = DNA  length = 286
FEATURE                Location/Qualifiers
source                 1..286
                       mol_type = genomic DNA
                       organism = Spinacia sp.
SEQUENCE: 68
tatatgttgc tgattaaata cgagactgat gatgatgatg atgtgtttat gggttttaaa  60
tcagattaaa tatatgggaa atgtaagtta atttgggatg cacataaggt gtttgctgaa  120
atgtctatga gaaatgttgt ttcttggact tagaatgata tacactgtcg tccattggtt  180
tccaatctta catttggttt gtgttttctt agtttgtttc tttaatcaac accaacccat  240
ttttttaaaa ctacctgcaa ctactaattt acgttgaccc tgtatc                 286

SEQ ID NO: 69          moltype = DNA  length = 119
FEATURE                Location/Qualifiers
source                 1..119
                       mol_type = genomic DNA
                       organism = Spinacia sp.
SEQUENCE: 69
gagaattaaa gactctgaca aaatgacaag tttgcccatg gggatgcagt acttaacctc  60
cctccaaacc ctcgaactat catattgtga tgaattgaat tcccttccag aatggataa   119

SEQ ID NO: 70          moltype = DNA  length = 122
FEATURE                Location/Qualifiers
source                 1..122
                       mol_type = genomic DNA
                       organism = Spinacia sp.
SEQUENCE: 70
gaacctcacc tcccttcaga cacttgggat atcggattgt ccagacctag ttaaaagatg  60
```

```
cagaaaaccc aacggcaagg actatcccaa aattcaacac atccccaaaa ttgtaagtca  120
tt                                                                 122

SEQ ID NO: 71          moltype = DNA  length = 325
FEATURE                Location/Qualifiers
source                 1..325
                       mol_type = genomic DNA
                       organism = Spinacia sp.
SEQUENCE: 71
gagattcctg gggttttctt tttgttgggg ttggatttca tgtatatgtt gctgattaaa  60
tacgagactg atgatgatga tgtgtttatg ggttttaaat cagattaaat atatgggaaa  120
tgcaagttaa tttgggatgc acataaggtg tttgctgaaa tgtctatgag aaatgttgtt  180
tcttggactt agaatgatat acactgtcgt cctttggttt ccaatcttac atttggtttg  240
tgttttctta gtttgtttct ttaatcaaca ccaacccgtt ttttttaaac tacctgcaac  300
tactaattta cgtttaccct gtatc                                        325

SEQ ID NO: 72          moltype = DNA  length = 119
FEATURE                Location/Qualifiers
source                 1..119
                       mol_type = genomic DNA
                       organism = Spinacia sp.
SEQUENCE: 72
gagaattaaa gactctgaca aaatgacaag tttgcccatg gggatgcagt acttaacctc  60
cctccaaacc ctcgaactat catattgtga tgaattgaat tcccttccag aatggataa   119

SEQ ID NO: 73          moltype = DNA  length = 122
FEATURE                Location/Qualifiers
source                 1..122
                       mol_type = genomic DNA
                       organism = Spinacia sp.
SEQUENCE: 73
gaacctcacc tcccttcaga cacttgggat atcggattgt ccagacctag ttaaaagatg  60
cagaaaaccc aacggcaagg actatcccaa aattcaacac atccccaaaa ttgtaagtca  120
tt                                                                 122

SEQ ID NO: 74          moltype = DNA  length = 242
FEATURE                Location/Qualifiers
source                 1..242
                       mol_type = genomic DNA
                       organism = Spinacia sp.
SEQUENCE: 74
atggggttgg atttcatgta tatgttgctg attaaatacg agactgatga tgatgatgtg  60
tttatgggtt ttaaatcaga ttaaatatat gggaaatgca agttaatttg ggatgcacat  120
aaggtgtttg ctgaaatgtc tatgagaaat gttgtttctt ggacttagaa tgatatacac  180
tgtcgtcctt tggtttccaa tcttacattt ggtttgtgtt ttcttagttt gtttcttgta  240
tc                                                                 242

SEQ ID NO: 75          moltype = DNA  length = 119
FEATURE                Location/Qualifiers
source                 1..119
                       mol_type = genomic DNA
                       organism = Spinacia sp.
SEQUENCE: 75
gagaattaaa gactctgaca aaatgacaag tttgcccatg gggatgcagt acttaacctc  60
cctccaaacc ctctatctac accattgtta tgaattgaat tcccttccag aatggataa   119

SEQ ID NO: 76          moltype = DNA  length = 122
FEATURE                Location/Qualifiers
source                 1..122
                       mol_type = genomic DNA
                       organism = Spinacia sp.
SEQUENCE: 76
gaacctcacc tcccttcaga gccttgtgat acggcggtgt ccagacctaa ttgaaagatg  60
cgaagaaccc aacggcgagg actatcccaa aattcgacac atctccagaa ttgtaagtca  120
tt                                                                 122

SEQ ID NO: 77          moltype = DNA  length = 326
FEATURE                Location/Qualifiers
source                 1..326
                       mol_type = genomic DNA
                       organism = Spinacia sp.
SEQUENCE: 77
gagattcctg gggttttttt tttcgttggg gttggttttc atgtatatgt tgctgattaa  60
atacgagact gatgatgatg atgtgtttat gggttttaaa tcagattaaa tatatgggaa  120
atgcaagtta atttgggatg cacataaggt gtttgctgaa atgtctatga gaaatgttgt  180
ttcttggact tagaatgata tacactgtcg tcctttggtt tccaatctta catttggttt  240
gtgttttctt agtttgtttc tttaatcaac accaacccgt tttttttaaa ctacctgcaa  300
ctactaattt acgtttaccc tgtatc                                       326
```